United States Patent
Day et al.

(10) Patent No.: US 6,793,839 B1
(45) Date of Patent: Sep. 21, 2004

(54) CUCURBITURILS AND METHOD FOR SYNTHESIS

(75) Inventors: Anthony Ivan Day, Captains Flat (AU); Alan Peter Arnold, Flynn (AU); John Rodney Blanch, Holt (AU)

(73) Assignee: Unisearch Limited, Sydney (AU)

( * ) Notice: Subject to any disclaimer, the term of this patent is extended or adjusted under 35 U.S.C. 154(b) by 0 days.

(21) Appl. No.: 09/959,770

(22) PCT Filed: May 5, 2000

(86) PCT No.: PCT/AU00/00412

§ 371 (c)(1),
(2), (4) Date: Jan. 7, 2002

(87) PCT Pub. No.: WO00/68232

PCT Pub. Date: Nov. 16, 2000

(30) Foreign Application Priority Data

May 7, 1999 (AU) .............................................. PQ0232

(51) Int. Cl.$^7$ ........................ C09K 3/00; C07D 487/04; C07D 487/22

(52) U.S. Cl. ........................ 252/1; 540/460; 548/302.1; 548/303.4

(58) Field of Search ................................ 540/456, 460; 548/302.1, 303.4

(56) References Cited

U.S. PATENT DOCUMENTS

| | | | | |
|---|---|---|---|---|
| 2,654,763 A | * | 10/1953 | Adkins | 548/303.4 |
| 3,203,960 A | * | 8/1965 | Gandon et al. | 548/303.4 |
| 3,252,901 A | * | 5/1966 | Zettler | 504/156 |
| 6,365,734 B1 | * | 4/2002 | Kim et al. | 540/460 |
| 6,639,069 B2 | * | 10/2003 | Kim et al. | 540/460 |
| 2002/0133003 A1 | | 9/2002 | Kim et al. | |

FOREIGN PATENT DOCUMENTS

| | | |
|---|---|---|
| DE | 40 01 139 | 10/1990 |
| DE | 196 03 377 | 8/1997 |

OTHER PUBLICATIONS

Translation of DE 4001139 (Jan. 25, 1999), Buschmann et al.*
Dantz, Dirk A. et al: "Complexation of volatile organic molecules from the gas phase with cucurbituril and beta—cyclodextrin", Supramolecular Chemistry (1998), 9(2), 79–83, XP008016079, whole article.
A. Flinn et al., "Decamethylcucurbit[5]uril", Angew. Chem. Int. Ed. Engl. 1992, 31, No. 11, pp. 1475–1477.
J.A.A.W. Elemans et al., "Bipyridine functionalized molecular chips. Self–assembly of their ruthenium complexes in water", Chemical Abstracts, Abstract No. 129:183422, 1998.
J. Kim et al., New Cucurbituril Homologues: Synthesis, Isolation, Characterization, and X–ray Crystal Structures of Cucurbit[n]uril (n=5, 7 and 8), J. Am. Chem. Soc. 2000, 122, pp. 540–541, Jan. 8, 2000.
H.J. Buschmann et al., "Cucurbituril as a ligand for the complexation of cations in aqueous solutions", Inorganica Chimica Acta, 193 (1992), pp. 93–97.
W.L. Mock in "Topics in Current Chemistry", 1995, 175, 1–24.

* cited by examiner

Primary Examiner—Matthew A. Thexton
(74) Attorney, Agent, or Firm—Stites & Harbison PLLC; B. Aaron Schulman

(57) ABSTRACT

A method for producing cucurbit[n]urils, where n is from 4 to 12, comprising mixing substituted and/or unsubstituted glycoluril with an acid and a compound that can form methylene bridges between glycoluril units, and heating the mixture to a temperature of from 20° to 120° to thereby form cucurbit[n]. Novel cucurbit[n]urils, where n=4, 5, 7, 8, 9, 10, 11 and 12 and substituted cucurbit[s,u]urils, where s=number of substituted glycoluril units, u=number of unsubstituted units and s+u=4–12 are also described.

104 Claims, 9 Drawing Sheets

1. F.G.M. Niele and R.J.M Nolte J. Am. Chem. Soc. 1988, 110, 172
2. J.W.H Smeets, R. P. Sijpesma, L. van Dalen, A.L. Spek, W.J.J. Smeets, and R.J.M Nolte,J. Org. Chem. 1989,54,3710.

Self condensation of either G1 or G2 or both.

Where n = y+ 2
cucurbit[n]uril

FORMULA 8

FORMULA 9

FORMULA 10

FORMULA 11

FORMULA 12    FORMULA 13    FORMULA 14

CUCURBITURILS AND METHOD FOR SYNTHESIS

The present invention relates to a method for preparing cucurbit[n]urils and cucurbit[s,u]urils. The present invention also relates to cucurbit[n]urils, to cucurbit[s,u]urils, and to a method of separating cucurbit[n]urils and/or cucurbit[s,u] urils. The present invention also relates to novel compounds used in the preparation of cucurbit[n]urils and cucurbit[s,u] urils.

Cucurbituril is the name given to a cyclic oligomer formed by linking six (6) glycoluril units via methylene bridges. Cucurbituril was first described in the literature in 1905 in a paper by R. Behrend, E. Meyer and F. Rusche, Leibigs Ann; Chem.; 339, 1, 1905. The macrocyclic structure of cucurbituril was first described in 1981 by W. A. Freeman et. al., "Cucurbituril", J. Am. Chem. Soc., 103 (1981). 7367–7368. Cucurbituril has a chemical formula of $C_{36}H_{36}N_{24}O_{12}$ and is a macrocyclic compound having a central cavity. An AM1 minimised structure of cucurbituril is shown in FIG. 1.

The internal cavity of cucurbituril has a diameter of about 550 pm, a depth of 650 pm with portals at either end about 400 pm across. This rigid cavity has been shown to have high selectively in binding a variety of medium-small molecules and in this regard reference is made to Cintas. P. J. Inclusion Phenomena and Molecular Recognition in Chemistry; 17, 205, 1994.

The preparation of cucurbituril has generally followed the procedure first described in the article by R. Behrend et. al. published in 1905.

In German patent no. DE 196 03377. published 7 Aug. 1997, a process for synthesising cucurbituril is described. This process includes dissolving acetylene diurea (glycoluril) in an aqueous solution of a strong mineral acid in the presence of excess formaldehyde, with warming. The water is evaporated from the mixture to completely eliminate the water from the mixture. The remaining polymer mixture is then heated to a temperature up to 145° C. to complete the reaction. The applicants for this patent have stated that a yield of up to 82.4% of the theoretical yield can be obtained.

In German patent no. DE 4001139, the use of cucurbituril to remove organic compounds with hydrophobic groups, dyes, decomposition products from dyes and/or heavy metals from aqueous solutions is described. The patent actually states that a cyclic oligomer which is obtained by condensation of urea, thiourea, derivates of urea and/or derivatives of the thiourea with dialdehydes and formaldehyde is used. Although the patent states that the degree of polymerisation, n, of the cyclic oligomer varies between about 3 and about 8, the examples of the patent showing cyclic oligomers having a degree of polymerisation, n, only of 6. Example 1 shows the preparation of cucurbituril by heating glycoluril under reflux with formaldehyde.

Experiments conducted by the present inventors in following the procedure of Example 1 of DE 4001139 have shown that cucurbituril having 6 glycoluril units joined together is formed. In the words of DE 4001139, n=6 for this product. No evidence was found of any cyclic oligomer having a degree of polymerisation, n, other than 6. Indeed, a paper by Buschmann et. al., Inorgica Chimica Acta, 1992, 193.93 states that under the synthetic conditions as described in DE 400 1139, only cucurbituril having a degree of polymerisation, n, of 6 is formed.

The present inventors have now developed a method for producing cucurbiturils having a degree of polymerization of 4 to 12. To assist in differentiating such compounds, the present inventors have adopted the terminology "cucurbit [n]uril" where n is a number from 4 to 12, to denote the different compounds. For example, a cyclic oligomer having 4 basic glycoluril (substituted or unsubstituted) units joined together would be denoted as "cucurbit[4]uril".

Figure 1:
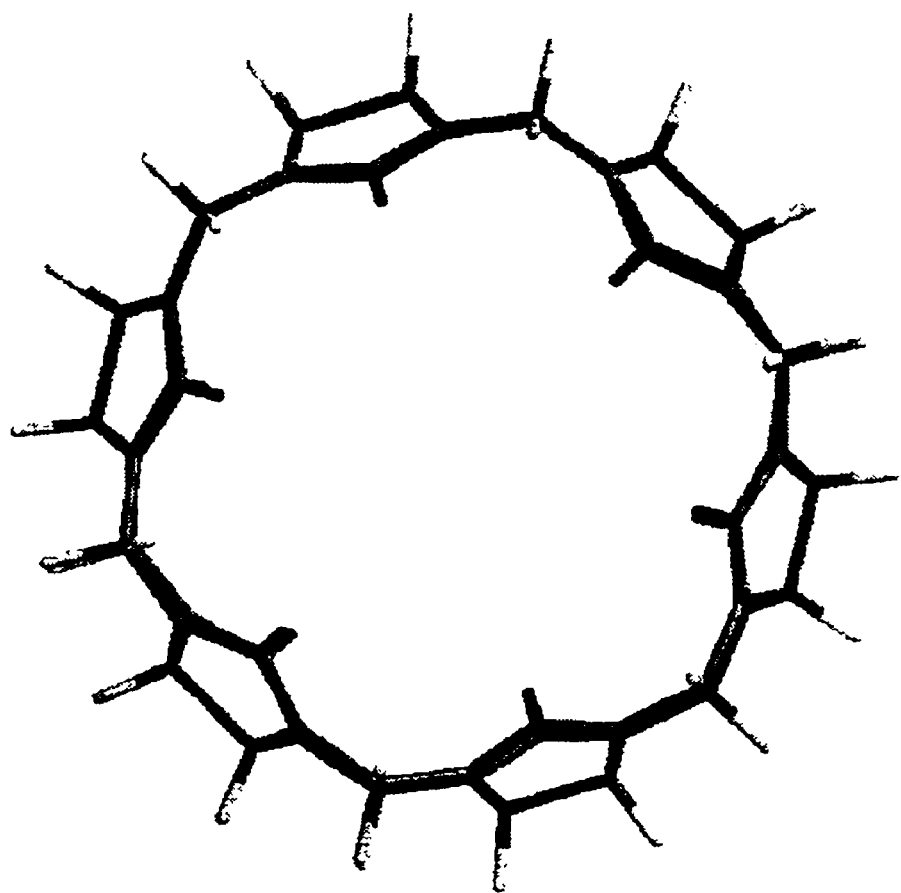
FIG. 1 shows an AM1 minimized structure of unsubstituted cucurbit[6]uril.
Figure 1A:
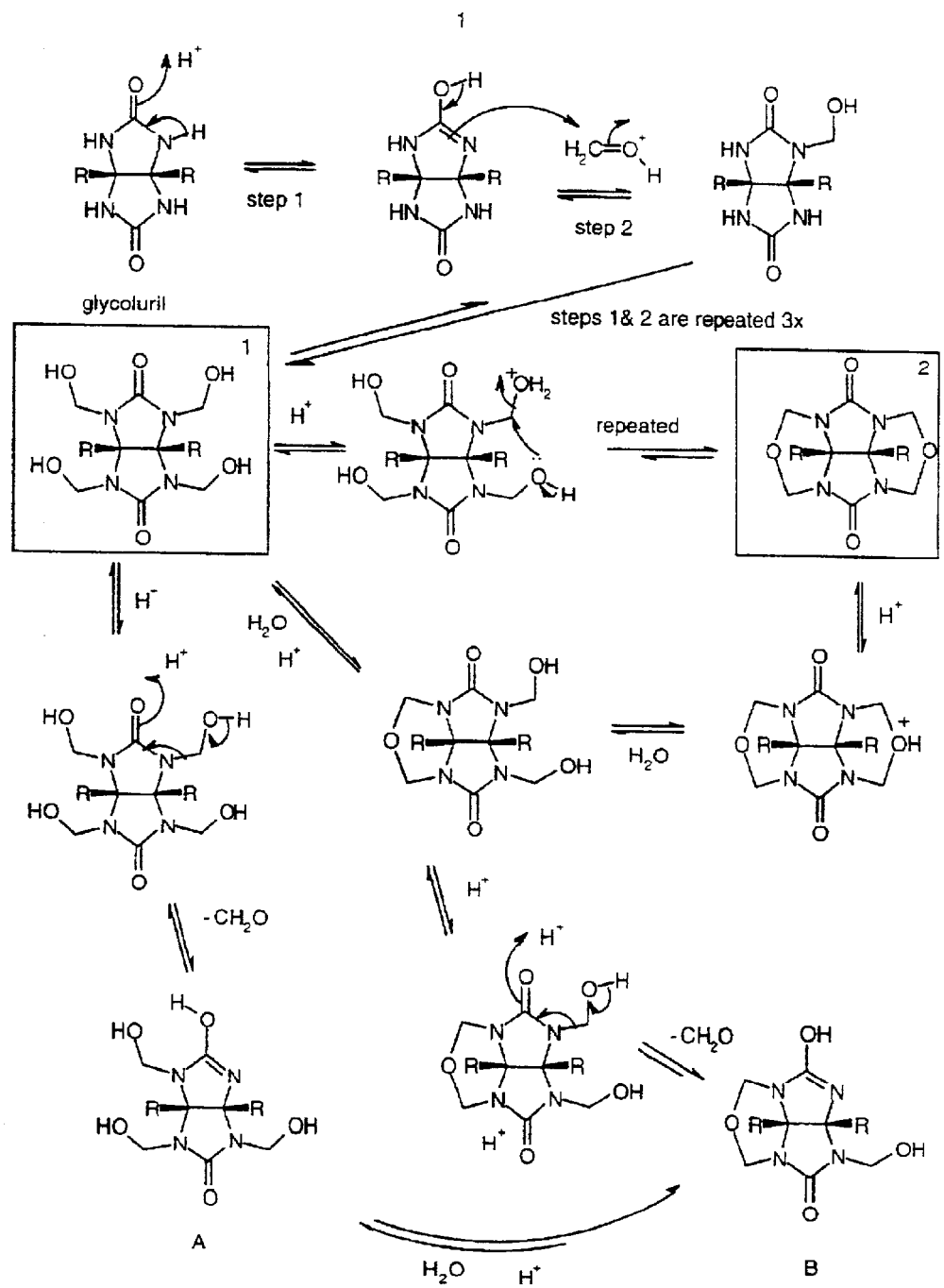
FIGS. 1a, 1b, 1c and 1d show a scheme for the proposed reaction mechanism for the synthesis of cucurbit[n]urils from substituted and/or unsubstituted glycoluril.
Figure 1B:
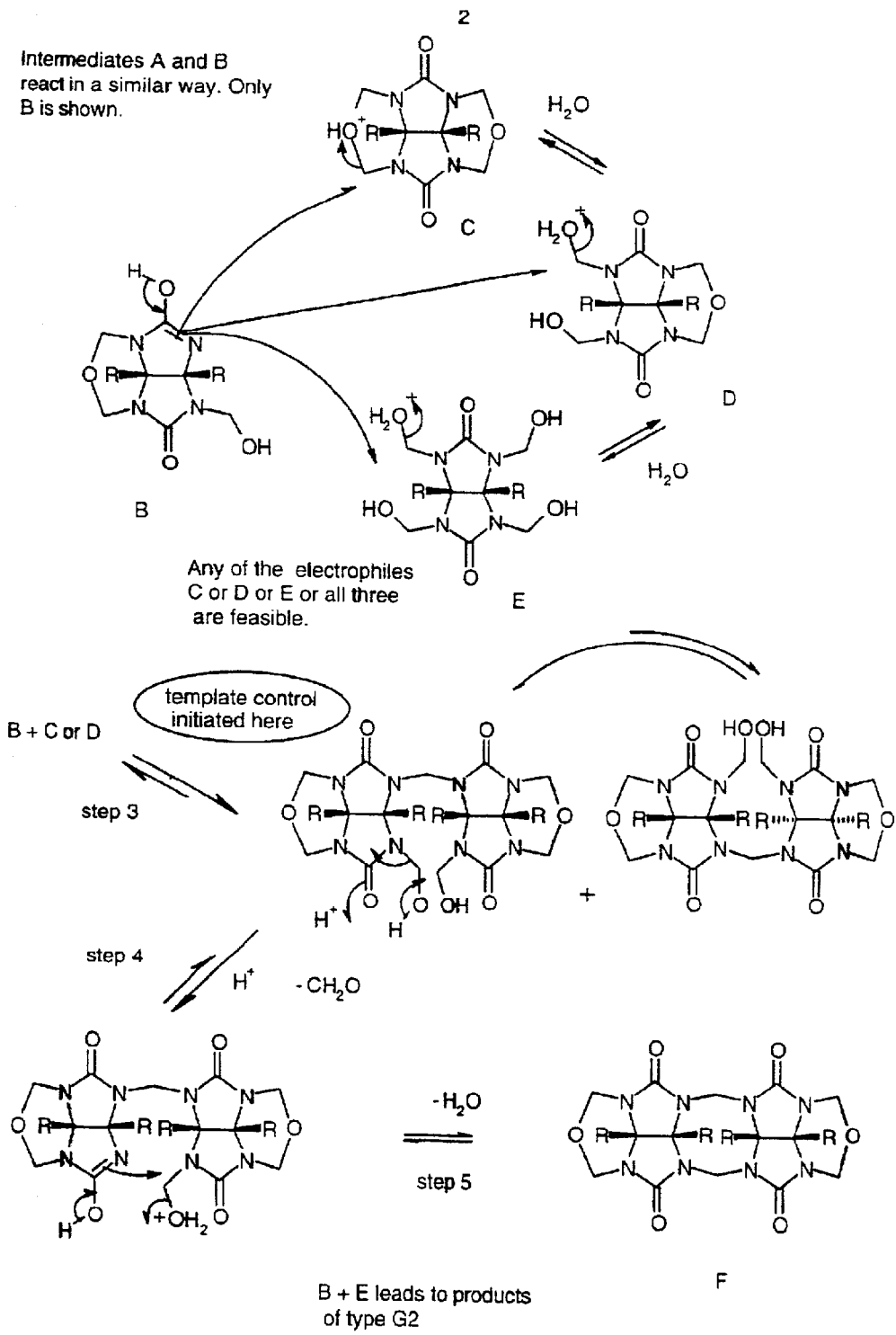
Figure 1C:
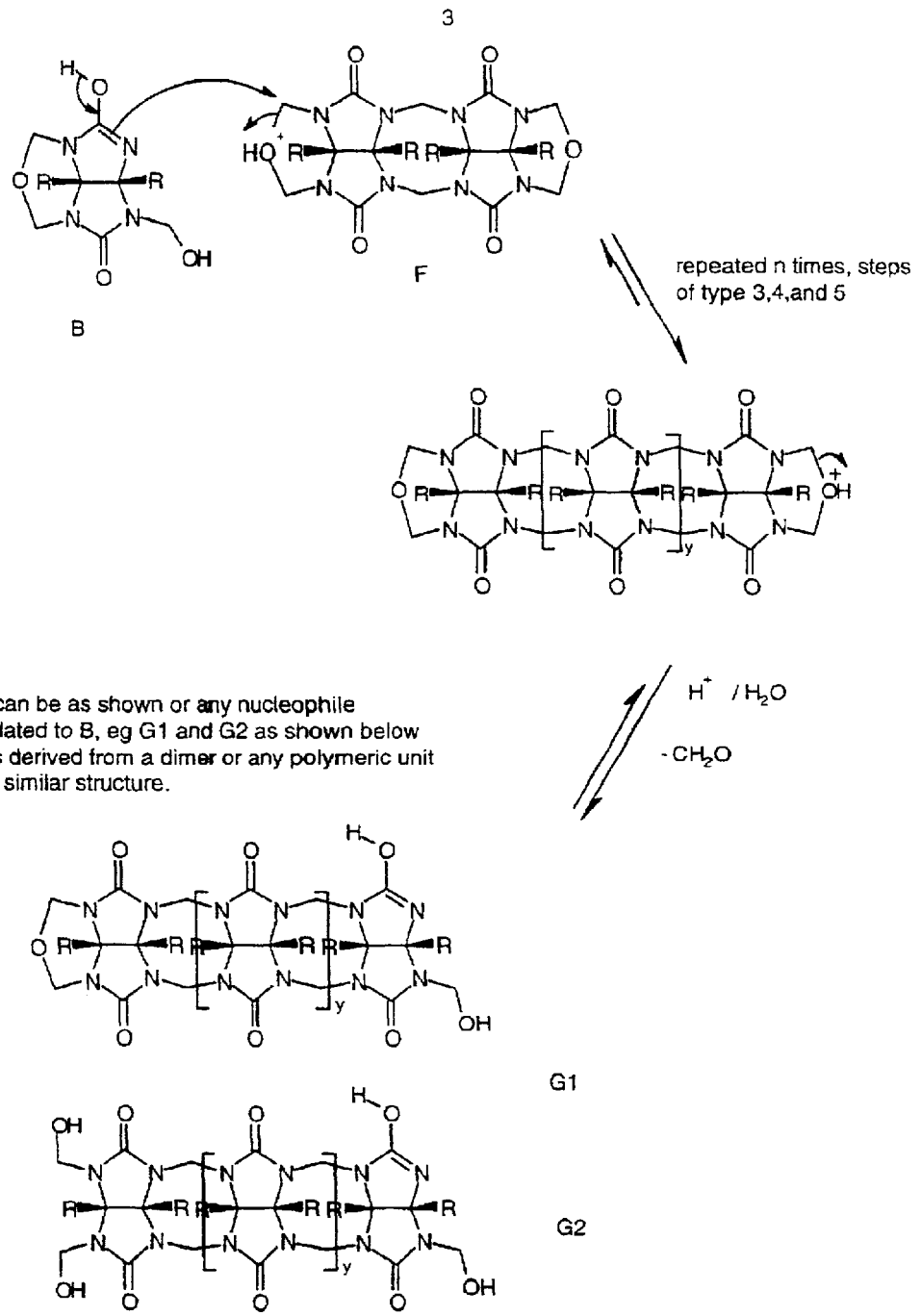
Figure 1D:
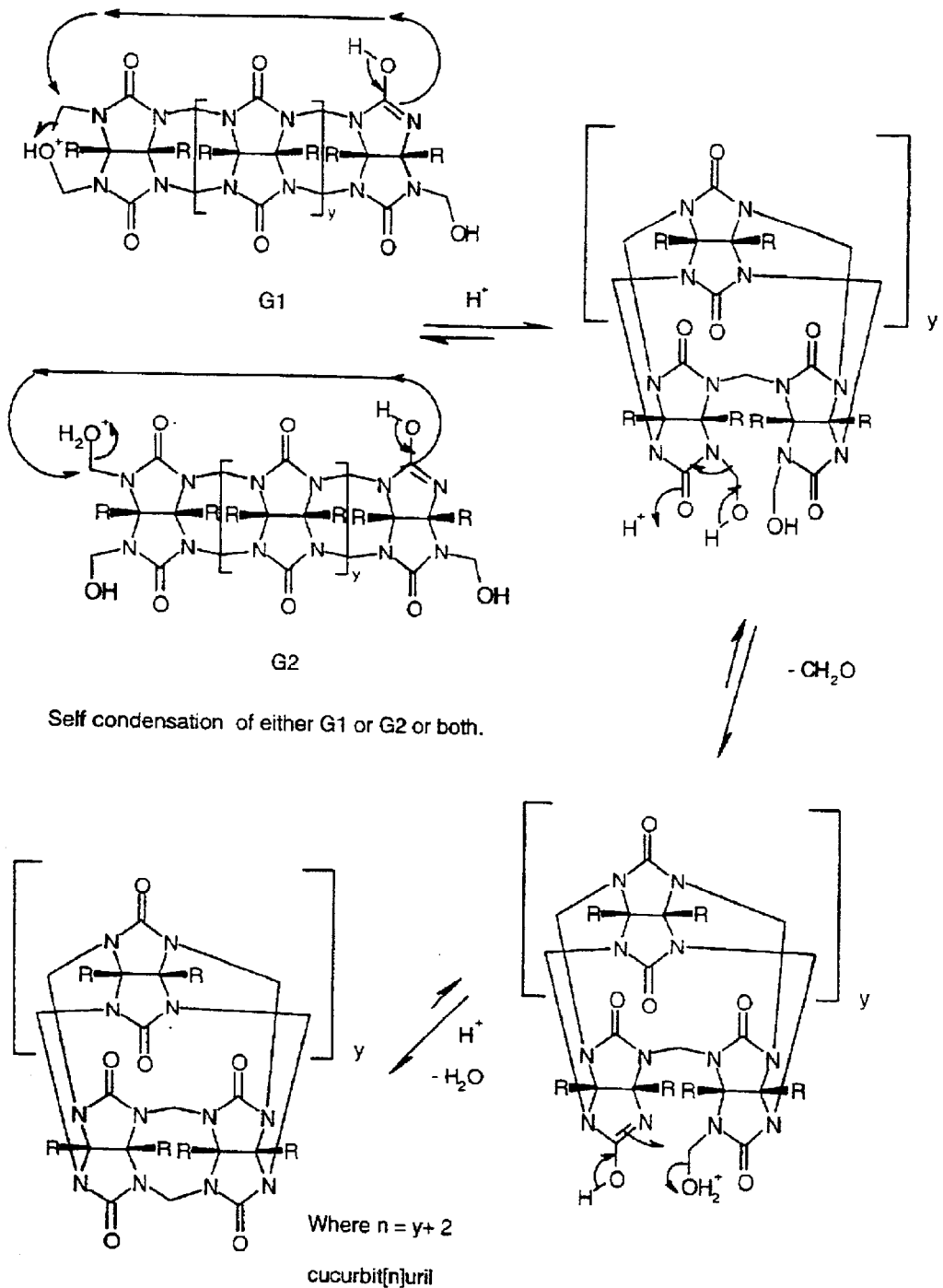
Figure 2:
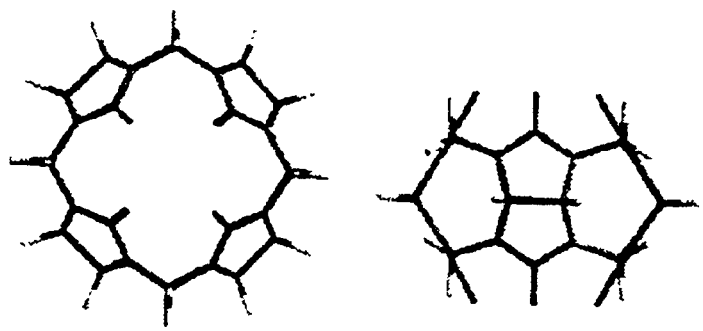
FIG. 2 shows the minimized chemical structure of unsubstituted cucurbit[4]uril prepared using PCT-Spartan.
Figure 3:
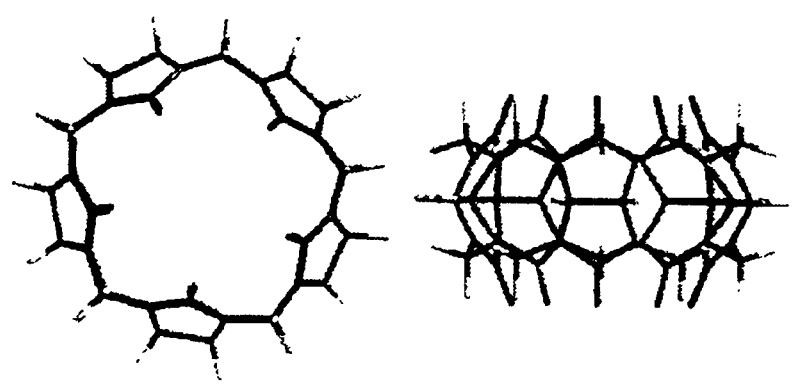
FIG. 3 shows the minimized chemical structure of unsubstituted cucurbit[5]uril prepared using PCT-Spartan.
Figure 4:
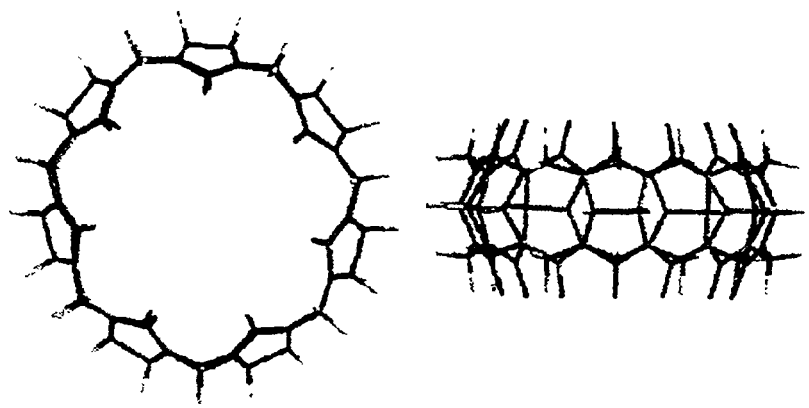
FIG. 4 shows the minimized chemical structure of unsubstituted cucurbit[7]uril prepared using PCT-Spartan.

In a first aspect, the present invention provides a method for producing cucurbit[n]urils, where n is from 4 to 12, comprising mixing substituted and/or unsubstituted glycoluril with an acid and a compound that can form methylene bridges between glycoluril units, and heating the mixture to a temperature of from 20° C. to 120° C. to thereby form cucurbit[n]urils. Preferably, n is from 5 to 10.

Preferably, the method of the present invention further comprises adding a salt to the mixture. It has been found that adding a salt to the mixture assists in achieving the synthesis of a variety of cucurbit[n]urils of differing unit sizes. Without wishing to be bound by theory, it is believed that an ion templating effect may be occurring. Thus, selection of the particular salt can control the amount of a derived cucurbit [n]uril in the product.

It has also been found that a number of other compounds can be added to the mixture in place of the salt, or in combination with the salt, to achieve the templating effect described above. The templating effect causes the relative amount of cucurbit[n]urils of differing unit sizes to be altered if the salt or other compound is added to the mixture. For example, the salt or other compound, when added to the reaction mixture, may alter, the ratio of, say, cucurbit[5]uril to cucurbit[6]uril, when that ratio is compared with the ratio of cucurbit[5]uril to cucurbit[6]uril that is produced using reaction mixtures having no salt or other compound added thereto but otherwise reacted under identical conditions.

For ease of description, such salts and other compounds will be described hereinafter throughout this specification as "templating compounds". In a preferred embodiment the method of the first aspect of the present invention further comprises adding one or more templating compounds to the mixture.

The templating compounds can be selected from a large number of compounds and indeed any compound that can alter the ratio of cucurbit[n]urils of different unit sizes produced in the method of the present invention can be used as a templating compound. The templating compound may be an organic compound, a salt of an organic compound, or an inorganic compound. Suitable compounds that may be used as a templating compound include ammonium chloride, lithium chloride, sodium chloride, potassium chloride, rubidium chloride, caesium chloride, ammonium chloride, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl)ethylenediamine, 2,2'-biquinoline, p-bromoaniline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobenzaldehyde, 2-aminobenzimidazole, bis-(4,4'-bipyridyl))-α,α'-p-xylene, red phosphorus, and lithium p-toluenesulfonate. The present inventors believe that a large number of other compounds could be suitable for use as templating compounds and therefore the above list should not be considered to be exhaustive. The anions of the acid may also be considered to be a template.

The templating compounds may be added singly to the reaction mixture or two or more templating compounds may be added to the reaction mixture.

If a salt is used as the templating compound salt that is added to the mixture is preferably a metal halide, ammonium halide, or the corresponding sulphates, or metal tosylates. It is preferred that the anion of the salt corresponds to the anion of the acid used. For example, where the acid used is hydrochloric acid, a metal chloride or ammonium chloride is the preferred salt. If sulphuric acid is used, metal sulphate or ammonium sulphate is the preferred salt. Similarly, iodide-containing salts are preferably used where hydriodic acid is the acid, and bromide-containing salts are preferably used where hydrobromic acid is used.

The acid is preferably a strong mineral acid or a strong organic acid. In principle, any acid can be used. The acid acts to catalyse the reactions taking place.

Preferred acids for use in the method of the first aspect of the present invention include sulfuric acid, hydrochloric acid, hydrobromic acid, hydroiodic acid, deuterated sulfuric acid, phosphoric acid, p-toluenesulfonic acid, and methane sulfonic acid. It will be appreciated that this list is not exhaustive and that any acid that can catalyse the reaction may be used in the method of the first aspect of the present invention.

It is especially preferred that the acid has a concentration of at least 5 M.

In some embodiments of the first aspect of the present invention, a solvent may also be added to the reaction mixture. The solvent is preferably selected from trifluoroacetic acid, methanesulfonic acid and 1,1,1-trifluorethanol.

The compound that can form methlene bridges between glycoluril units is most preferably formaldehyde, paraformaldehyde, trioxane or one or more precursors for formaldehyde. For convenience, the invention will hereinafter be described with reference to the case where formaldehyde is used.

The mixture is preferably heated to temperature of from 20° C. to 110° C. more preferably 60° C. to 110° C. most preferably from 80° C. to 110° C. It is preferred that boiling of the mixture is avoided. Heating under reflux, as required in the prior art, is not required (but may be used). Such temperature conditions are much milder than those utilised in the prior art synthesis process that led to the formation of cucurbit[6]uril. The prior art processes involved heating the mixture under reflux followed by heating to temperatures of up to 145 to 165° C. At room temperatures the present inventors have found that, cucurbit[n]uril was formed only if concentrated sulphuric acid w as used as the acid. It has been found that the mixture should generally he heated to a temperature of 60° C. and above to produce cucurbit[n]urils, with increased yields being obtained at temperatures on the range of 80° C. to 100° C.

The glycolurils that are used in the present invention have an unsubstituted structure as shown in formula 1 below:

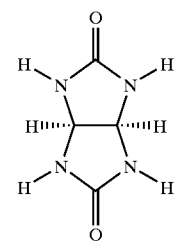

(Formula 1)

The general structure for the cucurbit[n]urils synthesised in accordance with the process of the present invention is shown in formula 2 below:

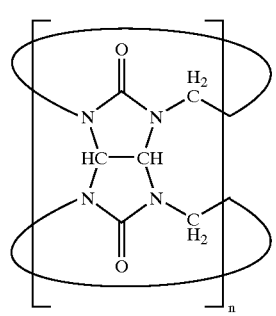

(Formula 2)

wherein n=4 to 12, preferably 4 to 10.

Substituted and unsubstituted glycolurils, or a mixture thereof, may be used to synthesise cucurbit[n]uril in accordance with the present invention. Substituted glycolurils have the general formula as shown in formula 3 below:

(Formula 3)

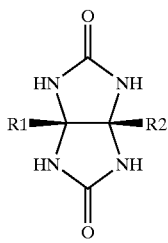

wherein $R_1$ and $R_2$ are the same or different and selected from an optionally substituted straight chain, branched or cyclic, saturated or unsaturated hydrocarbon radical or $R_1$ and $R_2$ form a cyclic hydrocarbon radical. The hydrocarbon radical for substituents $R_1$ and $R_2$ may include alkyl, alkenyl, alkynyl, aryl and heterocyclyl radicals. There are large numbers of substituted glycolurils known in the literature. Particular reference is made to a review article by Harro Petersen in Synthesis, 1973, 243–293, which contains a list of about 30 substituted glycolurils. The entire contents of this review article are hereby expressly incorporated into this specification by cross reference. The literature since the Petersen article has disclosed several other examples of substituted glycolurils and it is believed that essentially any α- or β-diketone could be used to make a glycoluril.

Investigations conducted by present inventors have shown that cucurbit[n]uril-like systems can be synthesised with many of the substituted glycolurils, preferably when used in comjuntion with unsubstituted glycolurils. The following substituted glycoluril compounds have been prepared adn used to synthesise substituted cucurbit[n]urils:

(Formula 4)

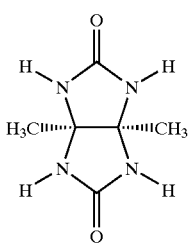

(Formula 5)

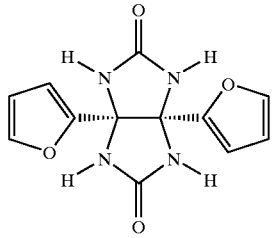

(Formula 6)

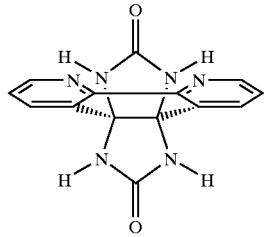

(Formula 7)

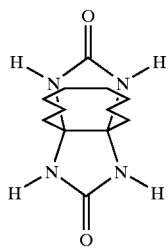

The compounds of formulae 5, 6 and 7 above are novel and accordingly, in another aspect, the present invention provides a substituted glycoluril compound of formula 5, formula 6 or formula 7.

The synthesis of substituted cucurbit[n]urils opens the possibility of being able to chemically link the substituted cucurbit[n]uril to a substrate or to chemisorb them onto a substrate. The solubility characteristics of the product may also be manipulated by selection of appropriate substituents.

As mentioned earlier, cucurbit[6]uril was first characterised and synthesised in 1905. However, the present inventors believe that cucurbit[n]uril, where n=4, 5, 7, 8, 9, 10, 11 or 12 has never previously been synthesised. Accordingly, in a further aspect, the present invention provides cucurbit[n]uril, where n=4, 5, 7, 8, 9, 10, 11 or 12. Preferably, n=5, 7, 8, 9 or 10.

The present also provides substituted cucurbit[n]urils, where n=4, 5, 6, 7, 8, 9, 10, 11 or 12. In order to clarify nomenclature when substituted cucurbiturils are formed, the present inventors have proposed that substituted cucurbiturils in accordance with the present invention be identified by the scheme "cucurbit[s,u]uril", where s=the number of substituted glycoluril units and u=the number of unsubstituted glycoluril units in the cucurbituril. Using this nomenclature, the present invention also provides cucurbit[s,u]uril, where s and u are as defined above and s+u=4 to 12, preferably 5 to 10.

In all of the experimental work conducted by the present inventors to date in relation to substituted cucurbiturils, the substituted cucurbiturils have incorporated both substituted and unsubstituted glycoluril units into the cucurbituril structure. Thus, it is preferred that u does not equal zero. If s equals zero, cucurbit[s,u]uril is equivalent to cucurbit[n]urils.

The substituted cucurbit[n]urils are preferably synthesized from substituted glycoluril or a mixture of substituted and unsubstituted glycoluril. The substituents may be as described above.

In order to show the structure of cucurbit[n]uril in cases where n=4, 5, 7 or 8, minimised chemical structures were prepared using PC-Spartan, a molecular modelling and visualisation package. The minimised structures are shown as formulae 8 to 11 in FIGS. 2 to 5:

The minimised structures of Formulae 8 to 11 clearly show the inner cavity of the cucurbituril. As the value of n increases, the size of the inner cavity increases, which enables different compounds to fit into the inner cavity.

The reaction product of the process of the present invention contains a mixture of different cucurbit[n]urils or cucurbit[s,u]urils. There are several methods that could be used to separate and purify these products and these are described below:

Successive Recrystallisation

All of the cucurbit[n]urils that have been observed are apparently soluble in acid solutions. Cucurbit[5 or 7 or 8 or 10]uril have been purified by successive recrystallisations from acid solutions. Because of the similar nature of the cucurbiturils, this is a slow process with more than 10 recrystallisations required to purify cucurbit[7]uril. As shown in the German patents cucurbit[6]uril can be obtained in a relatively pure state from a single recystallisation process.

Selective Dissolution/precipitation

We have been able to demonstrate that different cucurbiturils have markedly different solubilities in various salt solutions. It is possible to separate cucurbit[6]uril and cucurbit[7]uril from a mixture containing cucurbit[5–8]urils by dissolving cucurbit[6 or 7]uril out of the complex mixture using a 0.1M $Na_2SO_4$ solution.

We have also demonstrated the use of selective precipitation as a purification method. A solution of cucurbit[6]uril and cucurbit[7]uril was mixed with bis(4,4'-dipyridyl)-α,α'-p-xylene. $^1$H NMR showed a decrease in signal due to the cucurbit[7]uril and bis(4,4'-dipyridyl)-α,α'-p-xylene with several crystals depositing out of the sample.

According to another aspect, the present invention comprises separating a mixture of cucurbit[n]urils, where n=4 to 12, by mixing the mixture of cucurbit[n]urils with a salt solution in which at least one of the cucurbit[n]urils, but not all of the cucurbit[n]urils, dissolves and separating solids from the solution. Preferably, the method further comprising recovering at least one of the dissolved at least one cucurbit[n]urils from the solution. This method may also be used to separate mixtures of different substituted cucurbit[s,u]urils.

As an example, lithium chloride in hydrochloric acid solutions selectively assists the crystallisation of cucurbit[6]uril and cucurbit[8]uril leaving cucurbit[5]uril and cucurbit[7]uril in solution.

Potassium chloride, in hydrochloric acid solutions selectively assists the crystallisation of cucurbit[5]uril and cucurbit[8]uril leaving cucurbit[6]uril and cucurbit[7]uril in solution.

Any of the salt complexed cucurbitin[n]urils can be separated from their salt by a process of desalting on ion exchange resins such as Dowex 50. Dissolved in formic acid water, the mixtures are loaded onto the resin and the salts eluted with dilute hydrochloric acid/formic acid solutions until satisfactory salt removal and then the final recover, of the cucurbit[n]uril is achieved by elution with 5M or higher of aqueous hydrochloric acid.

Chromatographic Separation

Both Thin Layer Chromatography (TLC) and High Pressure Liquid Chromatography (HPLC) have demonstrated ability to separate out various oligomers of cucurbit[n]uril. Both of these systems are under continuing investigation. TLC using a silica stationary phase and 0.1M Hydrochloric acid as the mobile phase resulted in a mixture of cucurbit[n]urils separating into several bands. HPLC separation has been attempted using a C-18 stationary phase and 0.5M $Na_2SO_4$ mobile phase. The retention times of recrystallised samples of cucurbit[6]uril and cucurbit[7]uril were comparable with peaks found in mixed samples of crude cucurbit[n]urils.

In a further aspect, the present invention provides a method for separating a mixture of cucurbit[n]urils, where n=4 to 10, by dissolving the mixture of cucurbit[n]urils and subjecting the thus-formed solution of cucurbit[n]urils to chromatographic separation. This method may also be used to separate mixtures of cucurbit[s,u]urils.

In addition, polymer resins as chromatographic supports, such as. Dowex or Sephadex ion exchange columns or polyamines are effective in the purification of cucurbit[n]urils. The eluant most commonly used was 30–50% aqueous formic acid or a mixture of formic acid 98% and aqueous hydrochloric acid 0.5M in a ratio of 1:2 respectively. Samples sizes of 1 to 2 gm were able to be purified on a bed of 25 cm of resin.

In order to more fully understand the present invention, the proposed reaction mechanism will be discussed hereunder. It is to be understood that the following reaction mechanism is a proposed mechanism and the present invention should not be considered to be limited thereto. The proposed reaction mechanism hereunder should be read, in conjunction with FIGS. 1a, 1b, 1c and 1d.

The synthesis of cucurbit[n]uril or substituted cucurbit[n]uril (where n equals the number of glycouril units marking up cucurbituril) is an acid catalysed process. In the mechanism detailed below the first important intermediate 1 has been isolated and is the reaction of a glycouril with four equivalents of formaldehyde. The dehydration of this tetrol to the cyclic diether 2 has been demonstrated by the isolation of pure 2 where R=phenyl. The intermediates A or B are both produced through a series of acid catalysed steps. This mechanism is not prescriptive, as it is possible for either A or B to be produced without going through 1 or 2. Similarly, it is possible for glycouril units to begin linking on one side prior to reaction with formaldehyde on the other. This is a dynamic process with multiple reversible reaction steps. The mechanism shown here is only to be considered representative of the many possibilities.

The reaction from glycoluril to cucurbit[n]uril involves a number of intermediates produced through reversible reaction steps. The influences acting on the balance of these reversible steps are man, and some can be manipulated at a variety of points there by effecting the out come of the reaction.

EXAMPLES

The following examples illustrate preferred embodiments of the present invention:

Example 1

Synthesis of Cucurbit[n]urils 1.5 g—glycoluril 6.9 ml—mineral acid (hydrochloric 36%, hydrobromic 48%, hydriodic 47% or sulphuric acid 98% or 50%) or organic acid (para toluene sulphonic acid)

1.5 ml—aqueous formaldehyde 30%

5 mmol—of the corresponding alkali metal halide, ammonium halide or the corresponding sulphates in the case of sulphuric acid or alkali metal tosylates 600 mg—red phosphorus (this was added to reaction mixtures when hydriodic acid was used).

The glycoluril (1.5 gm, 10.6 mmol) was dissolved or suspended in the appropriate acid (6.9 ml. Then in the cases where a salt was used to manipulate reaction products the alkali metal ion or ammonium salt (5 mmol) with the corresponding anion appropriate to the acid was added. To this mixture at room temperature was added formaldehyde (1.5 ml) and within 5–10 min. the mixture set as a gel (note 1). After standing 3 hrs (note 2), heat was applied raising the temperature to 100° C. (note 3) whereby the gel liquefied. Heating and stirring was maintained for 2–3 hr (note 4). The reaction mixtures were cooled and in the case of HCl and HBr all volatiles were removed in vacuo at temperatures no higher than 50° C. The residues were dissolved in the appropriate acid and evaporated again, this was repeated twice (note 5).

For remaining acids, the products were isolated by adding methanol (10 ml) and collecting the resultant precipitate by filtration. The solid material was washed with methanol and acetone and air dried. The red phosphorus was removed by filtration before the addition of methanol.

Products have been isolated by a process of recrystallisation using hydrochloric acid or hydrobromic acid at varying concentrations to effect crystallisation. The total yield was >90% except in the case of hydriodic acid where yields were 30–80% depending on the salt used. In all cases the range of isomers was produced ie cucurbit[n]urils with n=4, 5, 6, 7, 8, 9, etc. The maximum production of each of these was achieved as follows:

n=4, <=1% in varying amounts under all conditions,
n=5, 55–75%, with NaI, KI, or RbI in hydriodic acid,
n=6, 80%, with CsCl in hydrochloric acid,
n=7, 52–65%, with no salts or with LiI in hydriodic acid,
n=8, 7–9%, with LiBr, or RbBr in hydrobromic acid, or LiOTs in aqueous pTsOH,
n=9, <=5%, with $NH_4Cl$ in hydrochloric acid,
n>=10, <=2%, in varying amounts under all conditions.

Notes A
1. Following the addition of formaldehyde there is an exothermic reaction. On larger scale the reaction mixture is cooled in an ice bath. Formaldehyde can be substituted by paraformaldehyde or trioxane or any formaldehyde producing precursor.
2. Proceeding to the next stage of the reaction procedure after 1 hr or 1 month at room temperature makes little difference to the out come except in the case of concentrated sulphuric acid where the reaction continues to cucurbit[n]urils at room temperature.
3. A reaction temperature of 60° C. and above is sufficient to give cucurbit[n]urils but at the lower temperatures with extended reaction times to achieve completion, up to 60hrs. The given yields above for the larger unit cucurbit[>=7]uril are on average increased a further 50% on the tabled yields.
4. In some cases pressure was generated during heating. In the event of a pressure build up the pressure was released
5. The repeated dissolving and evaporation was primarily carried out to remove excess formaldehyde and volatile formaldehyde by products.

Example 2
Synthesis Cucurbit[s,u]urils

The same templating controls are applied to substituted cucurbit[n]urils either by the above method where glycoluril used is substituted or as described below:

A mixture of tetracyclic ethers (2.5 mmol) and glycoluril (0.355 gm, 2.5 mmol) was dissolved or suspended in the appropriate acid (6.9 ml) (note 1). Then in the cases where a salt was used to manipulate reaction products the alkali metal ion or ammonium salt (5 mmol) with the corresponding anion appropriate to the acid was added. Heat was then applied to the reaction mixture, which was maintained at a temperature of 100° C. for 3hrs (Note 2). The reaction mixture was cooled to room temperature and the products were isolated by adding methanol (10 ml) and collecting the resultant precipitate by filtration. The solid material was washed with methanol and acetone and air dried. Further purification was effected by recrystalisation from aqueous hydrochloric acid or hydrobromic acid or dissolving in formic acid and precipitating by the addition of water.

The composition of these mixed substituted cucurbit[n] urils was determined by Electrospray Mass Spectroscopy.

Notes B
1. The tetracyclic ether refers to a compound of the formula shown in box 2 in FIG. 1a where the substituents R are alkyl aryl, phenanthroline or pyridyl.
2. Para toluene sulphonic acid was the acid of choice for the tetracyclic ethers where R equals aryl or pyridyl and the temperature of the reaction mixture was maintained at 110° C.
3.

Example 3
Analysis of Cucurbituril Mixture

Figure 5:
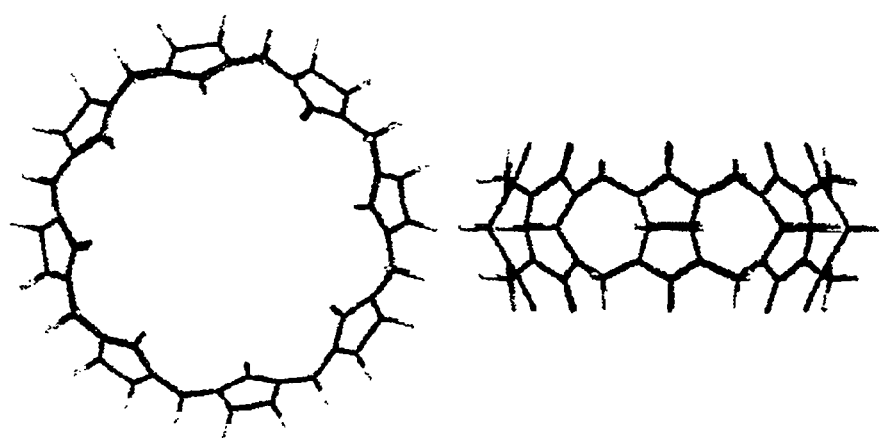
FIG. 5 shows the minimized chemical structure of unsubstituted cucurbit[8]uril prepared using PCT-Spartan.
Figure 5A:
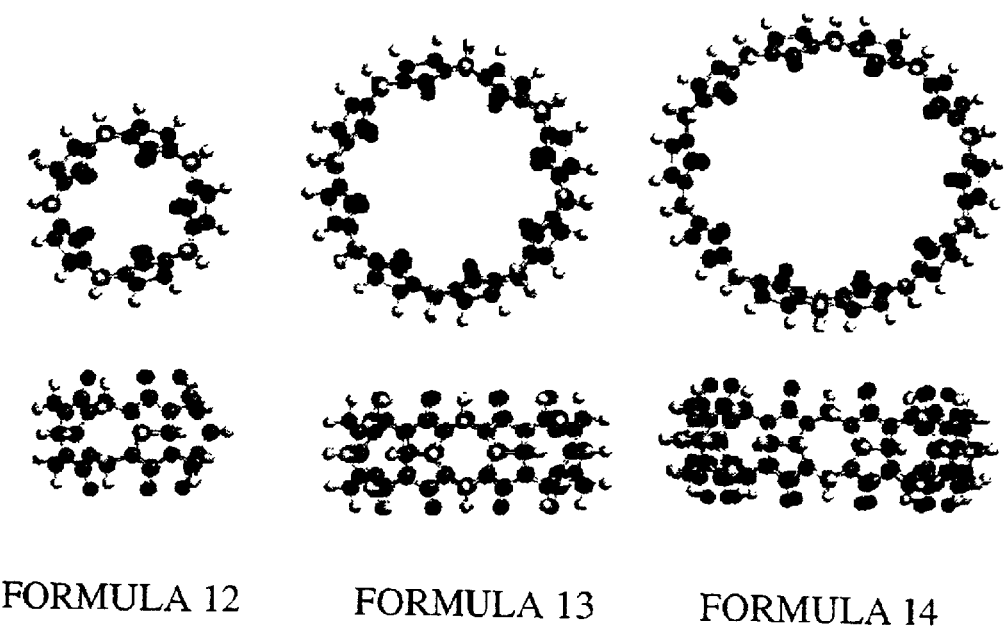
FIG. 5a shows models of the structure of unsubstituted curcurbit[5]uril, unsubstituted cucurbit[8]uril and unsubstituted cucurbit[10]uril as established by analysis of the X-ray crystal structure. Formula 12 is a model of the structure of unsubstituted cucurbit[5]uril, formula 13 is a model of the structure of unsubstituted cucurbit[8]uril and formula 14 is model of the structure of unsubstituted cucurbit[10]uril.

The analysis of the cucurbituril reaction mixture is routinely carried out by $^{13}C$ NMR. The present inventors have been able to achieve the x-ray crystal structure for cucurbit [5]uril. cucurbit[8]uril and cucurbit[10]uril. These are shown in FIG. 5a, in which Formula 12 is cucurbit[5]uril. Formula 13 is cucurbit[8]uril and Formula 14 is cucurbit [10]uril. Waters, salts etc of crystallisation are not shown.

(Cucurbit[6]uril is well established in the literature.) Solutions of pure cucurbit[7]uril, as determined by $^{13}C$ NMR have been prepared and Electro-Spray Mass Spectroscopy has confirmed the presence of only cucurbit[7]uril. (While pure cucurbit[7]uril is a crystalline material it is difficult to grow crystals of X-ray quality.) From these pure compounds the inventors have observed a trend in the $^{13}C$ NMR chemical shift of both the methylene and methine carbons of the cucurbit[n]uril. This trend has allowed us to identify cucurbit[9]uril, cucurbit[11]uril and cucurbit[12]uril in the reaction mixture. The table below shows the observed $^{13}C$ cehmical shifts for the unambiguously identified cucurbit[5] uril, cucurbit[6]uril, cucurbit[7]uril, cucurbit[8]uril and cucurbit[10]uril. The predicted and observed values for cucurbit[9]uril, cucurbit[11]uril, cucurbit[12]uril and cucurbit[13]uril are also provided.

| Curcurbit[n]uril n = | Methine C Observed* (ppm) | Methine C Calc'd (ppm) | Methylene C Observed* (ppm) | Methylene C Calc'd (ppm) |
|---|---|---|---|---|
| 4 | — | 68.54 | — | 48.75 |
| 5 | 69.84 | 69.87 | 50.58 | 50.68 |
| 6 | 70.98 | 70.96 | 52.29 | 52.17 |
| 7 | 71.90 | 71.88 | 53.48 | 53.43 |
| 8 | 72.70 | 72.68 | 54.49 | 54.53 |
| 9 | | 73.38 | | 55.49 |
| 10 | 73.98 | 74.01 | 56.32 | 56.35 |
| 11 | | 74.58 | | 57.13 |
| 12 | | 75.10 | | 57.84 |
| 13 | | 75.58 | | 58.50 |

*These values were recorded on pure isolated materials.

Figure 6:
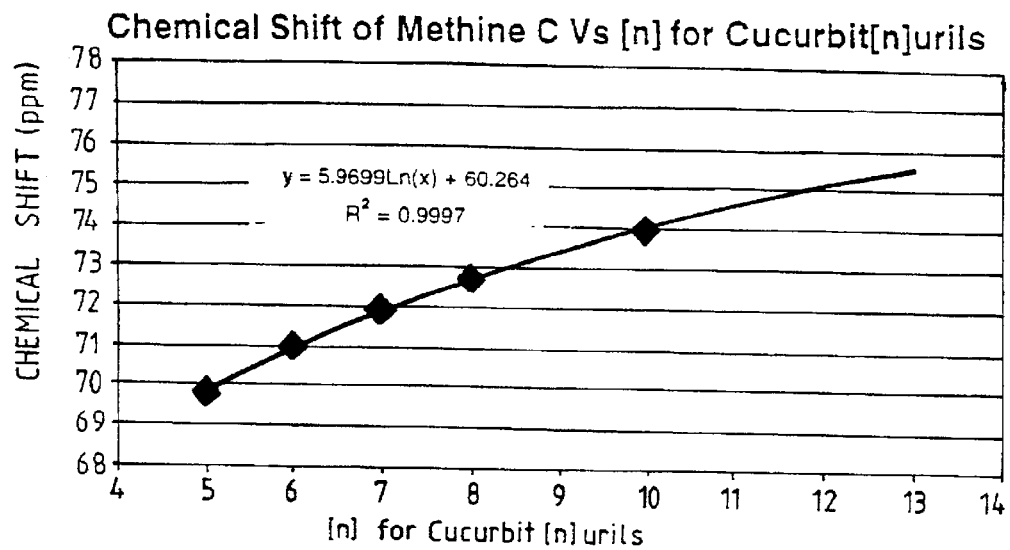
FIG. 6 is a graphical representation of the chemical shift of $C^{13}$ NMR resonances for the methine C for the unsubstituted cucurbit[6]uril, cucurbit[7]uril, cucurbit[8]uril and cucurbit[10uril, and the predicted values for unsubstituted cucurbit[9]uril, cucurbit[11]uril, cucurbit[11]uril, cucurbit [12]uril and cucurbit[13]uril.
Figure 7:
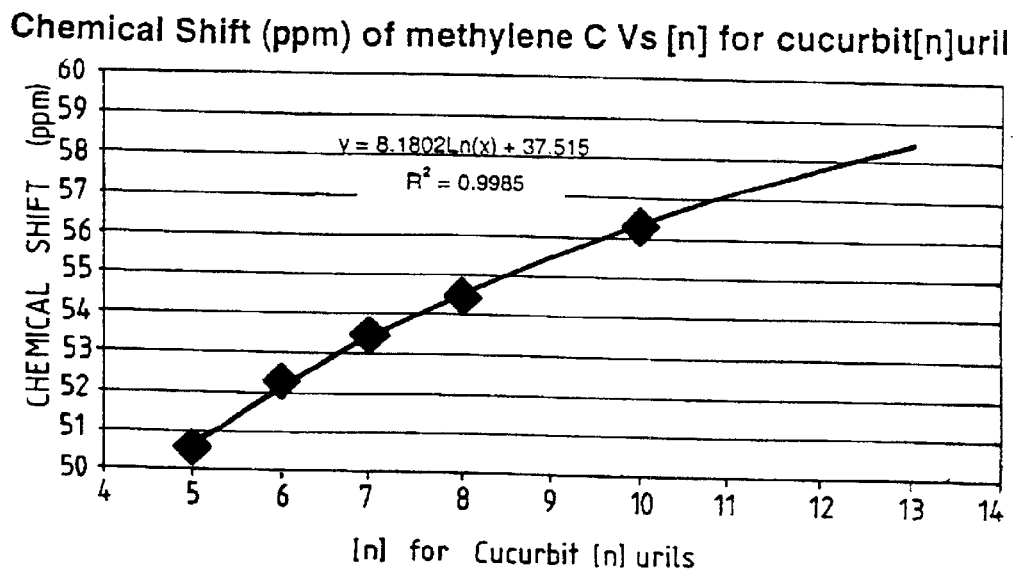
FIG. 7 is a graphical representation of the chemical shift of $C^{13}$ NMR resonances for the methylene C for the unsubstituted cucurbit[6]uril, cucurbit[7]uril, cucurbit[8]uril and cucurbit[10uril, and the predicted values for unsubstituted cucurbit[9]uril, cucurbit[11]uril, cucurbit[11]uril, cucurbit [12]uril and cucurbit[13]uril.

The results of this Table are graphically shown in FIGS. 6 and 7. Using this information the inventors have now identified cucurbit[9]uril (methine carbon 73.45 ppm and methylene carbon 55.42 ppm) in standard reaction mixtures. Cucurbit[11]uril and cucurbit[12]uril have only been observed by the methylene carbon when $^{13}C$ labelled formaldehyde was used as a reactant. Under these conditions the cucurbit[11]uril methylene carbon was observed at 56.86 ppm and the cucurbit[12]uril methylene carbon was observed at 57.75 ppm.

The inventors have routinely used the integration of $^{13}C$ NMR over the methine region of the spectra to determine the relative amounts of each cucurbit[n]uril in the mixture. In doing so it was assumed that the signal response for each species is related to the number of methine carbons for that cucurbit[n]uril and that there is little difference in signal response between the different cucurbit[n]urils. The integration-percent is then directly proportional to the mass percent of each component.

Example 4
Synthesis of Cucurbit[n]urils in Hydrochloric Acid.

Glycoluril (250 ml and hydrochloric acid (36% w/v, 2000 mL) were placed in a reaction flask. Formalin (40% w/v) (250 μL) was added in one portion and the reaction mixture heated to 100° C. for 15 hours. The reaction mixture was cooled and the products were collected by the removal of solvent on a rotary evaporator.

Yield ~30% by NMR

Approximate Yields by $^{13}$C NMR (% of recovered product)

| | |
|---|---|
| cucurbit[5]uril | 58% |
| cucurbit[6]uril | 42% |
| cucurbit[7]uril | % |
| cucurbit[8]uril | % |
| cucurbit[9]uril | <1% |
| cucurbit[10]uril | <1% |
| cucurbit[11]uril | <1% |

Example 5
Synthesis of Cucurbit[n]urils in Sulfuric Acid.

Glycoluril (500 mg) and sulfuric acid (9 M, 500 mL) were placed in a reaction flask. Formalin (40% w/v) (250 μL) was added in one portion and the reaction mixture heated to 100° C. for 15 hours. The reaction mixture was cooled and the products were precipitated by addition of methanol and Yield ~85% by NMR Approximate, Yields by $^{13}$C NMR (% of recovered product)

| | |
|---|---|
| cucurbit[5]uril | 21% |
| cucurbit[6]uril | 64% |
| cucurbit[7]uril | 14% |
| cucurbit[8]uril | 1% |
| cucurbit[9]uril | <1% |
| cucurbit[10]uril | <1% |
| cucurbit[11]uril | <1% |

Example 6
Synthesis of Cucurbit[n]urils in Sulfuric Acid.

Glycoluril (1.5 g) and sulfuric acid (9 M, 6.9 mL) were placed in a reaction flask. Formalin (40% w/v) (1.5 mL) was added in one portion and the reaction mixture heated to 100° C. for 3 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 26% |
| cucurbit[6]uril | 49% |
| cucurbit[7]uril | 19% |
| cucurbit[8]uril | 6% |
| cucurbit[9]uril | <1% |
| cucurbit[10]uril | <1% |
| cucurbit[11]uril | <1% |

Example 7
Synthesis of Cucurbit[n]urils in Hydrochloric Acid.

Glycoluril (77 mg) and hydrochloric acid (10 M, 0.4 mL) were placed in a reaction flask. Paraformaldehyde (33 mg) was added in one portion and the reaction mixture heated to 105° C. for 2.5 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 19% |
| cucurbit[6]uril | 54% |
| cucurbit[7]uril | 21% |
| cucurbit[8]uril | 6% |
| cucurbit[9]uril | <1% |
| cucurbit[10]uril | <1% |
| cucurbit[11]uril | <1% |

Example 8
Synthesis of Cucurbit[n]urils in Hydrochloric Acid.

Glycoluril (77 mg) and hydrochloric acid (9 M, 0.4 mL) were placed in a reaction flask. Paraformaldehyde (33 m) was added in one portion and the reaction mixture heated to 105° C. for 2.5 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 18% |
| cucurbit[6]uril | 56% |
| cucurbit[7]uril | 19% |
| cucurbit[8]uril | 6% |
| cucurbit[9]uril | <1% |
| cucurbit[10]uril | <1% |
| cucurbit[11]uril | <1% |

Example 9
Synthesis or Cucurbit[n]urils in Hydrochloric Acid.

Glycoluril (77 mg) and hydrochloric acid (8 M, 0.4 mL) were placed in a reaction flask. Paraformaldehyde (33 mg) was added in one portion and the reaction mixture heated to 105° C. for 2.5 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 15% |
| cucurbit[6]uril | 58% |
| cucurbit[7]uril | 23% |
| cucurbit[8]uril | 4% |
| cucurbit[9]uril | <1% |
| cucurbit[10]uril | <1% |
| cucurbit[11]uril | <1% |

Example 10
Synthesis of Cucurbit[n]urils in Hydrochloric Acid.

Glycoluril (77 m) and hydrochloric acid (7 M, 0.4 mL) were placed in a reaction flask. Paraformaldehyde (33 mg) was added in one portion and the reaction mixture heated to 105° C. for 2.5 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 18% |
| cucurbit[6]uril | 57% |
| cucurbit[7]uril | 23% |
| cucurbit[8]uril | 3% |
| cucurbit[9]uril | <1% |
| cucurbit[10]uril | <1% |
| cucurbit[11]uril | <1% |

Example 11
Synthesis of Cucurbit[n]urils in Hydrochloric Acid.

Glycoluril (77 mg) and hydrochloric acid (5 M, 0.4 mL) were placed in a reaction flask. Paraformaldehyde (33 mg) was added in one portion and the reaction mixture heated to 105° C. for 2.5 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 10% |
| cucurbit[6]uril | 60% |
| cucurbit[7]uril | 27% |
| cucurbit[8]uril | 3% |
| cucurbit[9]uril | <1% |
| cucurbit[10]uril | <1% |
| cucurbit[11]uril | <1% |

Example 12
Synthesis of Cucurbit[n]urils in Hydrochloric Acid.

Glycoluril (2.4 g) and hydrochloric acid (36% w/v, 2 mL) were placed in a reaction flask. Formalin (40% w/v) (2.4 mL) was added in one portion and the reaction mixture heated to 110° C. for 3 hours. The reaction mixture was cooled and the products were analysed by $^{13}$C NMR.

Yield >98% by NMR

Approximate Yields by 1$^{13}$C NMR (% of recovered product)

| | |
|---|---|
| cucurbit[5]uril | 6% |
| cucurbit[6]uril | 60% |
| cucurbit[7]uril | 30% |
| cucurbit[8]uril | 3% |
| cucurbit[9]uril | <1% |
| cucurbit[10]uril | <1% |
| cucurbit[11]uril | <1% |

Example 13
Synthesis of Cucurbit[n]urils in Hydrochloric Acid.

Glycoluril (2.4 g) and hydrochloric acid (36 w/v, 2 mL) were placed in a reaction flask. Formalin (40% w/v) (2.4 mL) was added in one portion and the reaction mixture heated to 110° C. for 18 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 6% |
| cucurbit[6]uril | 60% |
| cucurbit[7]uril | 30% |
| cucurbit[8]uril | 2% |
| cucurbit[9]uril | <1% |
| cucurbit[10]uril | <1% |
| cucurbit[11]uril | <1% |

Example 14
Synthesis of Cucurbit[n]urils in Hydrochloric Acid.

Glycoluril (2.1 g) and hydrochloric acid (36% w/v, 3 mL) were placed in a reaction flask. Paraformaldehyde (887 mg) was added in one portion and the reaction mixture heated to 110° C. for 18 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 9% |
| cucurbit[6]uril | 52% |
| cucurbit[7]uril | 29% |
| cucurbit[8]uril | 8% |
| cucurbit[9]uril | <1% |
| cucurbit[10]uril | <1% |
| cucurbit[11]uril | <1% |

Example 15
Synthesis of Cucurbit[n]urils in Hydrobromic Acid.

Glycoluril (2.1 g) and hydrobromic acid (48% w/v, 3 mL) were placed in a reaction flask. Paraformaldehyde (887 mg) was added in one portion and the reaction mixture heated to 100° C. for 18 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 8% |
| cucurbit[6]uril | 50% |
| cucurbit[7]uril | 29% |
| cucurbit[8]uril | 12% |
| cucurbit[9]uril | <1% |
| cucurbit[10]uril | <1% |
| cucurbit[11]uril | <1% |

Example 16
Synthesis of Cucurbit[n]urils in Hydrochloric Acid.

Glycoluril (105 mg) and hydrochloric acid (36% w/v, 0.4 mL) were placed in a reaction flask. Formalin (40% w/v) (105 μL) was added in one portion and the reaction mixture heated to 60° C. for 65 hours. The reaction mixture was cooled and the products were analysed by $^{13}$C NMR.

Yield >98% by NMR

Approximate Yields by $^{13}$C NMR (% of recovered product)

| | |
|---|---|
| cucurbit[5]uril | 4% |
| cucurbit[6]uril | 64% |
| cucurbit[7]uril | 23% |

-continued

| | |
|---|---|
| cucurbit[8]uril | 9% |
| cucurbit[9]uril | <1% |
| cucurbit[10]uril | <1% |
| cucurbit[11]uril | <1% |

Example 17
Synthesis of Cucurbit[n]urils in Hydrochloric Acid.

Glycoluril (77 m) and hydrochloric acid (8 M, 0.4 mL) were placed in a reaction flask. Paraformaldehyde (33 mg) was added in one portion and the reaction mixture heated to 105° C. for 2.5 hours. The reaction mixture was cooled and the products were analysed by $^{13}C$ NMR.

Yield >98% by NMR

Approximate Yields by $^{13}C$ NMR (% of recovered product)

| | |
|---|---|
| cucurbit[5]uril | 13% |
| cucurbit[6]uril | 60% |
| cucurbit[7]uril | 23% |
| cucurbit[8]uril | 10% |
| cucurbit[9]uril | <1% |
| cucurbit[10]uril | <1% |
| cucurbit[11]uril | <1% |

Example 18
Synthesis of Cucurbit[n]urils in Phosphoric Acid.

Glycoluril (1.5 g) and phosphoric acid (conc, 6.9 mL) were placed in a reaction flask. Formalin (40% w/v) (1.5 mL) was added in one portion and the reaction mixture heated to 100° C. for 18 hours. The reaction mixture was cooled and the products were analysed by $^{13}C$ NMR.

Yield >98% by NMR

Approximate Yields by $^{13}C$ NMR (% of recovered products

| | |
|---|---|
| cucurbit[5]uril | 10% |
| cucurbit[6]uril | 60% |
| cucurbit[7]uril | 28% |
| cucurbit[8]uril | <1% |
| cucurbit[9]uril | <1% |
| cucurbit[10]uril | <1% |
| cucurbit[11]uril | <1% |

Example 19
Synthesis of Cucurbit[n]urils in Hydrochloric Acid.

Glycoluril (1.02 g) and hydrochloric acid (36 w/v, 0.6 mL) were placed in a reaction flask. Paraformaldehyde (430 mg) was added in one portion and the reaction mixture heated to 100° C. for 15 hours. The reaction mixture was cooled and the products were analysed by $^{13}C$ NMR.

Yield >98% by NMR

Approximate Yields by $^{13}C$ NMR (% of recovered product)

| | |
|---|---|
| cucurbit[5]uril | 4% |
| cucurbit[6]uril | 53% |
| cucurbit[7]uril | 27% |
| cucurbit[8]uril | 10% |
| cucurbit[9]uril | <1% |
| cucurbit[10]uril | <1% |
| cucurbit[11]uril | <1% |

Example 20
Synthesis of Cucurbit[n]urils in Deuterated Sulfuric Acid.

Glycoluril (78 mg) and deuterated sulfuric acid (conc, 0.4 mL) were placed in a reaction flask. Formalin (40% w/v) (73 µL) was added in one portion and the reaction mixture heated to n° C. for 2 months. The reaction mixture was cooled and the products were analysed by $^{13}C$ NMR.

Yield >9% by NMR

Approximate Yields by $^{13}C$ NMR (% of recovered product)

| | |
|---|---|
| cucurbit[5]uril | <1% |
| cucurbit[6]uril | >95% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 21
Synthesis of Cucurbit[n]urils in Hydrochloric Acid.

Glycoluril (108 mg) and hydrochloric acid (36% w/v, 0.4 mL) were placed in a reaction flask. Formalin (40% w/v) (108 µL) was added in one portion kept at room temperature for month. The products were analysed by $^{13}C$ NMR.

Yield No cucurbiturils present NMR suggests oligomeric product.

Example 22
Synthesis of Cucurbit[n]urils in Hydrochloric Acid.

Glycoluril (1000 g) and hydrochloric acid (36% w/v, 1420 mL) were placed in a reaction flask. Paraformaldehyde (422 g) was added in one portion and the reaction mixture heated to 105° C. for 18 hours. The reaction mixture was cooled and the products were collected by the removal of solvent on a rotary evaporator.

Yield quantitative mass recovery and >98% cucurbit[n]urils by NMR

Approximate Yields by $^{13}C$ NMR (% of recovered product)

| | |
|---|---|
| cucurbit[5]uril | 19% |
| cucurbit[6]uril | 47% |
| cucurbit[7]uril | 27% |
| cucurbit[8]uril | 6% |
| cucurbit[9]uril | <1% |
| cucurbit[10]uril | <1% |
| cucurbit[11]uril | <1% |

Example 23
Synthesis of Cucurbit[n]urils in p-toluenesulfonic Acid.

Glycoluril (1 g) and p-toluenesulfonic acid (~90% w/w, 6.9 g) were placed in a reaction flask. Formalin (40% w/v) (1 mL mg) was added in one portion and the reaction mixture heated to 100° C. for 3 hours. The reaction mixture was cooled and the products were precipitated by addition of methanol and collected by vacuum filtration.

Yield >98% by NMR
Approximate Yields by $^{13}$C NMR (% of recovered product)

| | |
|---|---|
| cucurbit[5]uril | 6% |
| cucurbit[6]uril | 68% |
| cucurbit[7]uril | 20% |
| cucurbit[8]uril | 5% |
| cucurbit[9]uril | <1% |
| cucurbit[10]uril | <1% |
| cucurbit[11]uril | <1% |

Example 24
Synthesis of Cucurbit[n]urils in Methane Sulfonic Acid.

Glycoluril (146.5 mg) and methane sulfonic acid (neat, 1.5 mL) were placed in a reaction flask. Paraformaldehyde (65.5 mg) was added in one portion and the reaction mixture heated to 90° C. for 22 hours. The reaction mixture was cooled and the collected using a centrifuge. The collected solid was then dried at 80° C. overnight.

Yield >98% by NMR
Approximate Yields by $^{13}$C NMR (% of recovered product)

| | |
|---|---|
| cucurbit[5]uril | 6% |
| cucurbit[6]uril | 52% |
| cucurbit[7]uril | 33% |
| cucurbit[8]uril | 9% |
| cucurbit[9]uril | <1% |
| cucurbit[10]uril | <1% |
| cucurbit[11]uril | <1% |

Example 25
Synthesis of Cucurbit[n]urils in Methane Sulfonic Acid.

Glycoluril (197.6 mg) and methane sulfonic acid (neat, 1.5 mL) were placed in a reaction flask. Paraformaldehyde (91.1 mg) was added in one portion and the reaction mixture heated to 90° C. for 23.5 hours. The reaction mixture was cooled and the collected using a centrifuge. The collected solid was then dried at 80° C. overnight.

Yield >98% by NMR
Approximate Yields by $^{13}$C NMR (% of recovered product)

| | |
|---|---|
| cucurbit[5]uril | 8% |
| cucurbit[6]uril | 54% |
| cucurbit[7]uril | 30% |
| cucurbit[8]uril | 8% |
| cucurbit[9]uril | <1% |
| cucurbit[10]uril | <1% |
| cucurbit[11]uril | <1% |

Example 26
Synthesis of Cucurbit[n]urils in Methane Sulfonic Acid.

Glycoluril (302.6 mg) and methane sulfonic acid (neat, 1.5 mL) were placed in a reaction flask. Paraformaldehyde (130.3 mg) was added in one portion and the reaction mixture heated to 90° C. for 23.5 hours. The reaction mixture was cooled and the collected using a centrifuge. The collected solid was then dried at 80° C. overnight.

Yield >99% by NMR
Approximate Yields by $^{13}$C NMR (% of recovered product)

| | |
|---|---|
| cucurbit[5]uril | 3% |
| cucurbit[6]uril | 54% |
| cucurbit[7]uril | 32% |
| cucurbit[8]uril | 11% |
| cucurbit[9]uril | <1% |
| cucurbit[10]uril | <1% |
| cucurbit[11]uril | <1% |

Example 27
Synthesis of Cucurbit[n]urils in Methane Sulfonic Acid.

Glycoluril (497.3 mg) and methane sulfonic acid (neat, 1.5 mL) were placed in a reaction flask. Paraformaldehyde (204.0 mg) was added in one portion and the reaction mixture heated to 90° C. for 25 hours. The reaction mixture was cooled and the collected using a centrifuge. The collected solid was then dried at 80° C. overnight.

Yield >98% by NMR
Approximate Yields by $^{13}$C NMR (% of recovered product)

| | |
|---|---|
| cucurbit[5]uril | 0% |
| cucurbit[6]uril | 77% |
| cucurbit[7]uril | 23% |
| cucurbit[8]uril | 0% |
| cucurbit[9]uril | <1% |
| cucurbit[10]uril | <1% |
| cucurbit[11]uril | <1% |

Example 28
Synthesis of Cucurbit[n]urils in Methane Sulfonic Acid.

Glycoluril (144.6 mg) and methane sulfonic acid (neat, 1.5 mL) were placed in a reaction flask. Paraformaldehyde (61.3 mg) was added in one portion and the reaction mixture heated to 70° C. for 22.5 hours. The reaction mixture was cooled and the collected using a centrifuge. The collected solid was then dried at 80° C. overnight.

Yield >98% by NMR
Approximate Yields by $^{13}$C NMR (% of recovered product)

| | |
|---|---|
| cucurbit[5]uril | 0% |
| cucurbit[6]uril | 49% |
| cucurbit[7]uril | 34% |
| cucurbit[8]uril | 17% |
| cucurbit[9]uril | <1% |
| cucurbit[10]uril | <1% |
| cucurbit[11]uril | <1% |

Example 29
Synthesis of Cucurbit[n]urils in Methane Sulfonic Acid.

Glycoluril (145.2 mg) and methane sulfonic acid (neat, 1.5 mL) were placed in a reaction flask. Paraformaldehyde 162.9 mg) was added in one portion and the reaction mixture heated to 80° C. for 24 hours. The reaction mixture was cooled and the collected using a centrifuge. The collected solid was then dried at 80° C. overnight.

Yield >98% by NMR
Approximate Yields by $^{13}$C NMR (% of recovered product)

| | |
|---|---|
| cucurbit[5]uril | 4% |
| cucurbit[6]uril | 56% |
| cucurbit[7]uril | 28% |
| cucurbit[8]uril | 11% |
| cucurbit[9]uril | <1% |
| cucurbit[10]uril | <1% |
| cucurbit[11]uril | <1% |

Example 30
Synthesis of Cucurbit[n]urils in Methane Sulfonic Acid.

Glycoluril (142.5 mg) and methane sulfonic acid (neat, 1.5 mL) were placed in a reaction flask. Paraformaldehyde (60.7 m) was added in one portion and the reaction mixture heated to 100° C. for 25 hours. The reaction mixture was cooled and the collected using a centrifuge. The collected solid was then dried at 80° C. overnight.

Yield >98% by NMR

Approximate Yields by $^{13}$C NMR (% of recovered product)

| | |
|---|---|
| cucurbit[5]uril | 3% |
| cucurbit[6]uril | 59% |
| cucurbit[7]uril | 32% |
| cucurbit[8]uril | 6% |
| cucurbit[9]uril | <1% |
| cucurbit[10]uril | <1% |
| cucurbit[11]uril | <1% |

Example 31
Synthesis of Cucurbit[n]urils in Methane Sulfonic Acid.

Glycoluril (148.3 mg) and methane sulfonic acid (neat, 1.5 mL) were placed in a reaction flask. Paraformaldehyde (60.2 m,) was added in one portion and the reaction mixture heated to 110° C. for 27 hours. The reaction mixture was cooled and the collected using a centrifuge. The collected solid was then dried at 80° C. overnight.

Yield >98% by NMR

Approximate Yields by $^{13}$C NMR (% of recovered product)

| | |
|---|---|
| cucurbit[5]uril | 0% |
| cucurbit[6]uril | 93% |
| cucurbit[7]uril | 7% |
| cucurbit[8]uril | 0% |
| cucurbit[9]uril | <1% |
| cucurbit[10]uril | <1% |
| cucurbit[11]uril | <1% |

Example 32
Synthesis of Cucurbit[n]urils in Methane Sulfonic Acid Using o-carborane as an Added Template.

Glycoluril (146.9 mg), methane sulfonic acid (neat, 1.5 mL) and o-carborane (~18 mg) were placed in a reaction flask. Paraformaldehyde (64.2 mg) was added in one portion and the reaction mixture heated to 90° C. for 22.5 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 5% |
| cucurbit[6]uril | 52% |
| cucurbit[7]uril | 33% |
| cucurbit[8]uril | 10% |
| cucurbit[9]uril | <1% |
| cucurbit[10]uril | <1% |
| cucurbit[11]uril | <1% |

Example 33
Synthesis of Cucurbit[n]urils in Methane Sulfonic Acid Using o-carborane as an Added Template.

Glycoluril (200.5 mg), methane sulfonic acid (neat, 1.5 mL) and o-carborane (102.7 mg) were placed in a reaction flask. Paraformaldehyde (94.2 mg) was added in one portion and the reaction mixture heated to 90° C. for 24 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 8% |
| cucurbit[6]uril | 53% |
| cucurbit[7]uril | 29% |
| cucurbit[8]uril | 10% |
| cucurbit[9]uril | <1% |
| cucurbit[10]uril | <1% |
| cucurbit[11]uril | <1% |

Example 34
Synthesis of Cucurbit[n]urils in Methane Sulfonic Acid Using o-carborane as an Added Template.

Glycoluril (299.0 mg), methane sulfonic acid (neat, 1.5 mL) and o-carborane (152.4 mg) were placed in a reaction flask. Paraformaldehyde (126.2 mg) was added in one portion and the reaction mixture heated to 90° C. for 24 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 3% |
| cucurbit[6]uril | 57% |
| cucurbit[7]uril | 33% |
| cucurbit[8]uril | 7% |
| cucurbit[9]uril | <1% |
| cucurbit[10]uril | <1% |
| cucurbit[11]uril | <1% |

Example 35
Synthesis of Cucurbit[n]urils in Methane Sulfonic Acid Using o-carborane as an Added Template.

Glycoluril (501.9 mg), methane sulfonic acid (neat, 15 mL) and o-carborane (166.2 mg) were placed in a reaction flask. Paraformaldehyde (207.9 mg) was added in one portion and the reaction mixture heated to 90° C. for 25 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 0% |
| cucurbit[6]uril | 63% |
| cucurbit[7]uril | 28% |
| cucurbit[8]uril | 9% |
| cucurbit[9]uril | <1% |
| cucurbit[10]uril | <1% |
| cucurbit[11]uril | <1% |

Example 36
Synthesis of Cucurbit[n]urils in Methane Sulfonic Acid Using o-carborane as an Added Template.

Glycoluril (145.0 mg), methane sulfonic acid (neat, 1.5 mL) and o-carborane (53.4 mg) were placed in a reaction flask. Paraformaldehyde (62.5 mg) was added in one portion and the reaction mixture heated to 70° C. for 2.5 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 0% |
| cucurbit[6]uril | 48% |
| cucurbit[7]uril | 32% |
| cucurbit[8]uril | 20% |
| cucurbit[9]uril | <1% |
| cucurbit[10]uril | <1% |
| cucurbit[11]uril | <1% |

Example 37
Synthesis of Cucurbit[n]urils in Methane Sulfonic Acid Using o-carborane as an Added Template.

Glycoluril (146.9 mg), methane sulfonic acid (neat, 1.5 mL) and o-carborane (53.4 mg) were placed in a reaction flask. Paraformaldehyde (64.0 mg) was added in one portion and the reaction mixture healed to 80° C. for 24 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 4% |
| cucurbit[6]uril | 48% |
| cucurbit[7]uril | 29% |
| cucurbit[8]uril | 19% |
| cucurbit[9]uril | <1% |
| cucurbit[10]uril | <1% |
| cucurbit[11]uril | <1% |

Example 38
Synthesis of Cucurbit[n]urils in Methane Sulfonic Acid Using o-carborane as an Added Template.

Glycoluril (142.7 mg), methane sulfonic acid (neat, 1.5 mL) and o-carborane (48.6 mg) were placed in a reaction flask. Paraformaldehyde (60.7 mg) was added in one portion and the reaction mixture heated to 100° C. for 25 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 2% |
| cucurbit[6]uril | 53% |
| cucurbit[7]uril | 31% |
| cucurbit[8]uril | 14% |
| cucurbit[9]uril | <1% |
| cucurbit[10]uril | <1% |
| cucurbit[11]uril | <1% |

Example 39
Synthesis of Cucurbit[n]urils in Methane Sulfonic Acid Using o-carborane as an Added Template.

Glycoluril (145.5 mg), methane sulfonic acid (neat, 1.5 mL) and o-carborane (49.9 mg) were placed in a reaction flask. Paraformaldehyde (60.7 mg) was added in one portion and the reaction mixture heated to 110° C. for 27 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 0% |
| cucurbit[6]uril | 65% |
| cucurbit[7]uril | 26% |
| cucurbit[8]uril | 9% |
| cucurbit[9]uril | <1% |
| cucurbit[10]uril | <1% |
| cucurbit[11]uril | <1% |

Example 40
Synthesis of Cucurbit[n]urils in Hydrochloric Acid Using Thioacetamide as an Added Template.

Glycoluril (142.1 mg), hydrochloric acid (36% w/v 0.7 mL) and thioacetamide (12.8 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 0% |
| cucurbit[6]uril | 64% |
| cucurbit[7]uril | 36% |

-continued

| | |
|---|---|
| cucurbit[8]uril | 0% |
| cucurbit[9]uril | <1% |
| cucurbit[10]uril | <1% |
| cucurbit[11]uril | <1% |

Example 41
Synthesis of Cucurbit[n]urils in Hydrochloric Acid Using N-(1-napthyl)ethylenediamine as an Added Template.

Glycoluril (142.1 mg), hydrochloric acid (36% w/v, 0.7 mL) and N-(1-napthyl)ethylenediamine (44.1 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 12% |
| cucurbit[6]uril | 53% |
| cucurbit[7]uril | 23% |
| cucurbit[8]uril | 12% |
| cucurbit[9]uril | <1% |
| cucurbit[10]uril | <1% |
| cucurbit[11]uril | <1% |

Example 42
Synthesis of Cucurbit[n]urils in Hydrochloric Acid Using 2,2'-biquinoyl as an Added Template.

Glycoluril (142.1 mg), hydrochloric acid (36% w/v, 0.7 mL) and 2,2'-biquinoyl (43.6 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 6% |
| cucurbit[6]uril | 62% |
| cucurbit[7]uril | 26% |
| cucurbit[8]uril | 6% |
| cucurbit[9]uril | <1% |
| cucurbit[10]uril | <1% |
| cucurbit[11]uril | <1% |

Example 43
Synthesis of Cucurbit[n]urils in Hydrochloric Acid Using p-bromoaniline as an Added Template.

Glycoluril (142.1 mg), hydrochloric acid (36% w/v, 0.7 mL) and p-bromoaniline (29.3 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 11% |
| cucurbit[6]uril | 36% |
| cucurbit[7]uril | 36% |
| cucurbit[8]uril | 15% |
| cucurbit[9]uril | <1% |
| cucurbit[10]uril | <1% |
| cucurbit[11]uril | <1% |

Example 44
Synthesis of Cucurbit[n]urils in Hydrochloric Acid Using Tetrabutylammonium Chloride as an Added Template.

Glycoluril (142.1 mg), hydrochloric acid (36% w/v, 0.7 mL) and tetrabutylammonium chloride (47.3 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 5% |
| cucurbit[6]uril | 55% |
| cucurbit[7]uril | 25% |
| cucurbit[8]uril | 5% |
| cucurbit[9]uril | <1% |
| cucurbit[10]uril | <1% |
| cucurbit[11]uril | <1% |

Example 45
Synthesis of Cucurbit[n]urils in Hydrochloric Acid Using Taurine as an Added Template.

Glycoluril (142.1 mg), hydrochloric acid (36% w/v, 0.7 mL) and taurine (1.3 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 16% |
| cucurbit[6]uril | 51% |
| cucurbit[7]uril | 23% |
| cucurbit[8]uril | 10% |
| cucurbit[9]uril | <1% |
| cucurbit[10]uril | <1% |
| cucurbit[11]uril | <1% |

Example 46
Synthesis of Cucurbit[n]urils in Hydrochloric Acid Using Blue Tetrazolium as an Added Template.

Glycoluril (142.1 mg, hydrochloric acid (36% w/v, 0.7 mL) and blue tetrazolium (123.7 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 7% |
| cucurbit[6]uril | 55% |
| cucurbit[7]uril | 23% |
| cucurbit[8]uril | 10% |
| cucurbit[9]uril | <1% |
| cucurbit[10]uril | <1% |
| cucurbit[11]uril | <1% |

Example 47

Synthesis of Cucurbit[n]urils in Hydrochloric Acid Using 2-amino-3-methyl benzoic acid as an Added Template.

Glycoluril (142.1 mg), hydrochloric acid (36% w/v, 0.7 mL) and 2-amino-3-methyl benzoic acid (25.7 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 5% |
| cucurbit[6]uril | 55% |
| cucurbit[7]uril | 25% |
| cucurbit[8]uril | 5% |
| cucurbit[9]uril | <1% |
| cucurbit[10]uril | <1% |
| cucurbit[11]uril | <1% |

Example 48

Synthesis of Cucurbit[n]urils in Hydrochloric Acid Using indol-3-aldehyde as an Added Template.

Glycoluril (142.1 mg), hydrochloric acid (36% w/v, 0.7 mL) and indol-3-aldehyde (24.7 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 3% |
| cucurbit[6]uril | 70% |
| cucurbit[7]uril | 25% |
| cucurbit[8]uril | 2% |
| cucurbit[9]uril | <1% |
| cucurbit[10]uril | <1% |
| cucurbit[11]uril | <1% |

Example 49

Synthesis of Cucurbit[n]urils in Hydrochloric Acid Using Cystine as an Added Template.

Glycoluril (142.1 mg), hydrochloric acid (36% w/v, 0.7 mL) and cystine (40.9 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 5% |
| cucurbit[6]uril | 55% |
| cucurbit[7]uril | 25% |
| cucurbit[8]uril | 5% |
| cucurbit[9]uril | <1% |
| cucurbit[10]uril | <1% |
| cucurbit[11]uril | <1% |

Example 50

Synthesis of Cucurbit[n]urils in Hydrochloric Acid Using p-acetamidoaniline as an Added Template.

Glycoluril (142.1 mg), hydrochloric acid (36% w/v, 0.7 mL) and p-acetamidoaniline (25.5 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 5% |
| cucurbit[6]uril | 55% |
| cucurbit[7]uril | 25% |
| cucurbit[8]uril | 5% |
| cucurbit[9]uril | <1% |
| cucurbit[10]uril | <1% |
| cucurbit[11]uril | <1% |

Example 51

Synthesis of Cucurbit[n]urils in Hydrochloric Acid Using p-amninophenol as an Added Template.

Glycoluril (142.1 mg), hydrochloric acid (36% w/v, 0.7 mL) and p-aminophenol (18.6 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 13% |
| cucurbit[6]uril | 39% |
| cucurbit[7]uril | 36% |
| cucurbit[8]uril | 12% |
| cucurbit[9]uril | <1% |
| cucurbit[10]uril | <1% |
| cucurbit[11]uril | <1% |

Example 52
Synthesis of Cucurbit[n]urils in Hydrochloric Acid Using Acetamide as an Added Template.

Glycoluril (142.1 mg), hydrochloric acid (36% w/v, 0.7 mL) and acetamide (10.0 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 9% |
| cucurbit[6]uril | 31% |
| cucurbit[7]uril | 39% |
| cucurbit[8]uril | 17% |
| cucurbit[9]uril | <1% |
| cucurbit[10]uril | <1% |
| cucurbit[11]uril | <1% |

Example 53
Synthesis of Cucurbit[n]urils in Hydrochloric Acid Using 4-aminoacetophenone as an Added Template.

Glycoluril (142.1 mg), hydrochloric acid (36% w/v, 0.7 mL) and 4-aminoacetophenone (23.0 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 9% |
| cucurbit[6]uril | 44.5% |
| cucurbit[7]uril | 35% |
| cucurbit[8]uril | 12% |
| cucurbit[9]uril | <1% |
| cucurbit[10]uril | <1% |
| cucurbit[11]uril | <1% |

Example 54
Synthesis of Cucurbit[n]urils in Hydrochloric Acid Using 4-dimethylaminobenzaldehyde as an Added Template.

Glycoluril (142.1 mg), hydrochloric acid (36% w/v, 0.7 mL) and 4-dimethylaminobenzaldehyde (25.4 mg) were placed in a reaction flask. Paraformaldehyde (60.0 mg) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 5% |
| cucurbit[6]uril | 55% |
| cucurbit[7]uril | 25% |
| cucurbit[8]uril | 5% |
| cucurbit[9]uril | <1% |
| cucurbit[10]uril | <1% |
| cucurbit[11]uril | <1% |

Example 55
Synthesis of Cucurbit[n]urils in Hydrochloric Acid Using 2-aminobenzimadazol as an Added Template.

Glycoluril (142.1 mg), hydrochloric acid (36% w/v, 0.7 mL) and 2-aminobenzimadazol (22.6 mg) were placed in a reaction flask. Paraformaldehyde (60.0 mg) was added in one portion and the reaction mixture heated to 95° C. for 2 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 9% |
| cucurbit[6]uril | 40% |
| cucurbit[7]uril | 30% |
| cucurbit[8]uril | 11% |
| cucurbit[9]uril | <1% |
| cucurbit[10]uril | <1% |
| cucurbit[11]uril | <1% |

Example 56
Synthesis of Cucurbit[n]urils in Hydrochloric Acid Using bis-(4,4'-bipyridyl)-α,α'-p-xylene as an Added Template.

Glycoluril (142.1 mg), hydrochloric acid (36% w/v, 0.7 mL) and bis-(4,4'-bipyrndyl)-α,α'-p-xylene (110.8 mg) were placed in a reaction flask. Paraformaldehyde (60.0 mg) was added in one portion and the reaction mixture heated to 95° C. for 2 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 8% |
| cucurbit[6]uril | 42% |
| cucurbit[7]uril | 46% |
| cucurbit[8]uril | 5% |
| cucurbit[9]uril | <1% |
| cucurbit[10]uril | <1% |
| cucurbit[11]uril | <1% |

Example 57
Synthesis of Cucurbit[n]urils in Hydrochloric Acid Using Tetraethylammonium Chloride as an Added Template.

Glycoluril (142.1 mg), hydrochloric acid (36% w/v, 0.7 mL) and tetraethylammonium chloride (28.2 mg) were placed in a reaction flask. Paraformaldehyde (60.0 mg) was added in one portion and the reaction mixture heated to 95° C. for 2 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 0% |
| cucurbit[6]uril | 10% |
| cucurbit[7]uril | 70% |
| cucurbit[8]uril | 18% |
| cucurbit[9]uril | <1% |
| cucurbit[10]uril | <1% |
| cucurbit[11]uril | <1% |

Example 58
Synthesis of Cucurbit[n]urils in Hydrochloric Acid Using Ammonium Chloride as an Added Template.

Glycoluril (1.49 g), hydrochloric acid (36% w/v, 6.9 mL) and ammonium chloride (280 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 15% |
| cucurbit[6]uril | 62% |
| cucurbit[7]uril | 20% |
| cucurbit[8]uril | 3% |
| cucurbit[9]uril | <1% |
| cucurbit[10]uril | <1% |
| cucurbit[11]uril | <1% |

Example 59
Synthesis of Cucurbit[n]urils in Hydrochloric Acid Using Lithium Chloride as an Added Template.

Glycoluril (1.49 g), hydrochloric acid (36% w/v, 6.9 mL) and lithium chloride (211 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 7% |
| cucurbit[6]uril | 68% |
| cucurbit[7]uril | 22% |
| cucurbit[8]uril | 3% |
| cucurbit[9]uril | <1% |
| cucurbit[10]uril | <1% |
| cucurbit[11]uril | <1% |

Example 60
Synthesis of Cucurbit[n]urils in Hydrochloric Acid Using Sodium Chloride as an Added Template.

Glycoluril (1.49 g), hydrochloric acid (36% w/v, 6.9 mL) and sodium chloride (292 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 3% |
| cucurbit[6]uril | 73% |
| cucurbit[7]uril | 21% |
| cucurbit[8]uril | 3% |
| cucurbit[9]uril | <1% |
| cucurbit[10]uril | <1% |
| cucurbit[11]uril | <1% |

Example 61
Synthesis of Cucurbit[n]urils in Hydrochloric Acid Using Potassium Chloride as an Added Template.

Glycoluril (1.49 g), hydrochloric acid (36% w/v, 6.9 mL) and potassium chloride (372 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 24% |
| cucurbit[6]uril | 61% |
| cucurbit[7]uril | 14% |
| cucurbit[8]uril | 2% |
| cucurbit[9]uril | <1% |
| cucurbit[10]uril | <1% |
| cucurbit[11]uril | <1% |

Example 62
Synthesis of Cucurbit[n]urils in Hydrochloric Acid Using Rubidium Chloride as an Added Template.

Glycoluril (1.49 g), hydrochloric acid (36% w/v, 6.9 mL) and rubidium chloride (604 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 14% |
| cucurbit[6]uril | 70% |
| cucurbit[7]uril | 15% |
| cucurbit[8]uril | <1% |
| cucurbit[9]uril | <1% |
| cucurbit[10]uril | <1% |
| cucurbit[11]uril | <1% |

Example 63
Synthesis of Cucurbit[n]urils in Hydrochloric Acid Using Caesium Chloride as an Added Template.

Glycoluril (1.49 g) hydrochloric acid (36% w/v, 6.9 mL) and caesium chloride (842 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| cucurbit[5]uril | 4% |
|---|---|
| cucurbit[6]uril | 79% |
| cucurbit[7]uril | 16% |
| cucurbit[8]uril | 1% |
| cucurbit[9]uril | <1% |
| cucurbit[10]uril | <1% |
| cucurbit[11]uril | <1% |

Example 64
Synthesis of Cucurbit[n]urils in Hydrobromic Acid Using Ammonium Bromide as an Added Template.

Glycoluril (1.49 g), hydrobromic acid (48% w/v, 6.9 mL) and ammonium bromide (490 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| cucurbit[5]uril | 8% |
|---|---|
| cucurbit[6]uril | 66% |
| cucurbit[7]uril | 23% |
| cucurbit[8]uril | 3% |
| cucurbit[9]uril | <1% |
| cucurbit[10]uril | <1% |
| cucurbit[11]uril | <1% |

Example 65
Synthesis of Cucurbit[n]urils in Hydrobromic Acid.

Glycoluril (1.49 g) and hydrobromic acid (48% w/v, 6.9 mL) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| cucurbit[5]uril | 5% |
|---|---|
| cucurbit[6]uril | 59% |
| cucurbit[7]uril | 30% |
| cucurbit[8]uril | 5% |
| cucurbit[9]uril | <1% |
| cucurbit[10]uril | <1% |
| cucurbit[11]uril | <1% |

Example 66
Synthesis of Cucurbit[n]urils in Hydrobromic Acid Using Lithium Bromide as an Added Template.

Glycoluril (1.49 g) hydrobromic acid (48% w/v, 6.9 mL) and lithium bromide (435 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| cucurbit[5]uril | 7% |
|---|---|
| cucurbit[6]uril | 49% |
| cucurbit[7]uril | 36% |
| cucurbit[8]uril | 7% |
| cucurbit[9]uril | <1% |
| cucurbit[10]uril | <1% |
| cucurbit[11]uril | <1% |

Example 67
Synthesis of Cucurbit[n]urils in Hydrobromic Acid Using Sodium Bromide as an Added Template.

Glycoluril (1.49 g), hydrobromic acid (48% w/v, 6.9 mL) and sodium bromide (515 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| cucurbit[5]uril | 16% |
|---|---|
| cucurbit[6]uril | 44% |
| cucurbit[7]uril | 35% |
| cucurbit[8]uril | 5% |
| cucurbit[9]uril | <1% |
| cucurbit[10]uril | <1% |
| cucurbit[11]uril | <1% |

Example 68
Synthesis of Cucurbit[n]urils in Hydrobromic Acid Using Sodium Bromide, as an Added Template.

Glycoluril (1.49 g), hydrobromic acid (48% w/v, 6.9 mL) and sodium bromide (5000 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| cucurbit[5]uril | 40% |
|---|---|
| cucurbit[6]uril | 51% |
| cucurbit[7]uril | 9% |
| cucurbit[8]uril | <1% |
| cucurbit[9]uril | <1% |
| cucurbit[10]uril | <1% |
| cucurbit[11]uril | <1% |

Example 69
Synthesis of Cucurbit[n]urils in Hydrobromic Acid Using Potassium Bromide as an Added Template.

Glycoluril (1.49 g) hydrobromic acid (48% w/v, 6.9 mL) and potassium bromide (595 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 36% |
| cucurbit[6]uril | 44% |
| cucurbit[7]uril | 18% |
| cucurbit[8]uril | 2% |
| cucurbit[9]uril | <1% |
| cucurbit[10]uril | <1% |
| cucurbit[11]uril | <1% |

Example 70
Synthesis of Cucurbit[n]urils in Hydrobromic Acid Using Rubidium Bromide as an Added Template.

Glycoluril (1.49 g), hydrobromic acid (48% w/v, 6.9 mL) and rubidium bromide (827 mg) were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 25% |
| cucurbit[6]uril | 43% |
| cucurbit[7]uril | 24% |
| cucurbit[8]uril | 8% |
| cucurbit[9]uril | <1% |
| cucurbit[10]uril | <1% |
| cucurbit[11]uril | <1% |

Example 71
Synthesis of Cucurbit[n]urils in Hydrobromic Acid Using Caesium Bromide as an Added Template.

Glycoluril (1.49 g), hydrobromic acid (48% w/v, 6.9 mL) and caesium bromide (1070 mg were placed in a reaction flask. Formalin (40% w/v) (1.5 mL) was added in one portion and the reaction mixture heated to 100° C. for 3 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 15% |
| cucurbit[6]uril | 59% |
| cucurbit[7]uril | 23% |
| cucurbit[8]uril | 3% |
| cucurbit[9]uril | <1% |
| cucurbit[10]uril | <1% |
| cucurbit[11]uril | <1% |

Example 72
Synthesis of Cucurbit[n]urils in Hydrochloric Acid Using Ammonium Chloride as an Added Template.

Glycoluril (1.49 g), hydrochloric acid (36% w/v, 6.9 mL) and ammonium chloride (280 mg) were placed in a reaction flask. Formalin (40% w/v) (1.5 mL) was added in one portion and the reaction mixture heated to 60° C. for 60 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 11% |
| cucurbit[6]uril | 60% |
| cucurbit[7]uril | 21% |
| cucurbit[8]uril | 8% |
| cucurbit[9]uril | <1% |
| cucurbit[10]uril | <1% |
| cucurbit[11]uril | <1% |

Example 73
Synthesis of Cucurbit[n]urils in Hydrobromic Acid Using Rubidium Bromide as an Added Template.

Glycoluril (1.49 g), hydrobromic acid (48% w/v, 6.9 mL) and rubidium bromide (827 mg). were placed in a reaction flask. Formalin (40% w/v) (1.5 mL) was added in one portion and the reaction mixture heated to 60° C. for 84 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 34% |
| cucurbit[6]uril | 39% |
| cucurbit[7]uril | 19% |
| cucurbit[8]uril | 9% |
| cucurbit[9]uril | <1% |
| cucurbit[10]uril | <1% |
| cucurbit[11]uril | <1% |

Example 74
Synthesis of Cucurbit[n]urils in Hydrochloric Acid Using Potassium Chloride as an Added Template.

Glycoluril (250 g), hydrochloric acid (36% w/v, 6.9 mL) and potassium chloride (62 g) were placed in a reaction flask. Paraformaldehyde (110 g) was added in one portion and the reaction mixture heated to 95° C. for 4 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 39% |
| cucurbit[6]uril | 36% |
| cucurbit[7]uril | 20% |
| cucurbit[8]uril | 5% |
| cucurbit[9]uril | <1% |
| cucurbit[10]uril | <1% |
| cucurbit[11]uril | <1% |

Example 75
Synthesis of Cucurbit[n]urils in Hydrochloric Acid Using Potassium Chloride as an Added Template.

Glycoluril (8 g), hydrochloric acid (36% w/v, 6.9 mL) and potassium chloride (2.1 g) were placed in a reaction flask. Paraformaldehyde (3.5 g) was added in one portion and the reaction mixture heated to 100° C. for 3.5 hours. The reaction mixture was cooled and the products were collected by the removal of solvent on a rotary evaporator and analysed by NMR.

Yield >98% by NMR

Approximate Yields by $^{13}$C NMR (mass % of recovered product)

| | |
|---|---|
| cucurbit[5]uril | 26% |
| cucurbit[6]uril | 56% |
| cucurbit[7]uril | 15% |
| cucurbit[8]uril | 3% |
| cucurbit[9]uril | <1% |
| cucurbit[10]uril | <1% |
| cucurbit[11]uril | <1% |

Example 76
Synthesis of Cucurbit[n]urils in Hydrobromic Acid Using Lithium Bromide as an Added Template.

Glycoluril (1.49 g), hydrobromic acid (48% w/v, 6.9 mL) and lithium bromide (4.3 g) were placed in a reaction flask. Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 13% |
| cucurbit[6]uril | 63% |
| cucurbit[7]uril | 22% |
| cucurbit[8]uril | 3% |
| cucurbit[9]uril | <1% |
| cucurbit[10]uril | <1% |
| cucurbit[11]uril | <1% |

Example 77
Synthesis of Cucurbit[n]urils in Hydroiodic Acid.

Glycoluril (1.49 g) and hydroiodic acid (57% w/v, 6.9 mL) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield 2.2 g

Approximate Yields by $^{13}$C NMR (mass % of recovered product)

| | |
|---|---|
| cucurbit[5]uril | 3% |
| cucurbit[6]uril | 72% |
| cucurbit[7]uril | 22% |
| cucurbit[8]uril | 3% |
| cucurbit[9]uril | <1% |
| cucurbit[10]uril | <1% |
| cucurbit[11]uril | <1% |

Example 78
Synthesis of Cucurbit[n]urils in Hydroiodic Acid Using Lithium Iodide as an Added Template.

Glycoluril (1.49 g), hydroiodic acid (57% w/v, 6.9 mL) and lithium iodide (665 mg) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield 0.9 g

Approximate Yields by $^{13}$C NMR (mass % of recovered product)

| | |
|---|---|
| cucurbit[5]uril | 16% |
| cucurbit[6]uril | 28% |
| cucurbit[7]uril | 56% |
| cucurbit[8]uril | <1% |
| cucurbit[9]uril | <1% |
| cucurbit[10]uril | <1% |
| cucurbit[11]uril | <1% |

Example 79
Synthesis of Cucurbit[n]urils in Hydroiodic Acid Using Sodium Iodide as an Added Template.

Glycoluril (1.49 g) hydroiodic acid (57% w/v, 6.9 mL) and sodium iodide (745 mg) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 19% |
| cucurbit[6]uril | 55% |
| cucurbit[7]uril | 17% |
| cucurbit[8]uril | 9% |
| cucurbit[9]uril | <1% |
| cucurbit[10]uril | <1% |
| cucurbit[11]uril | <1% |

Example 80
Synthesis of Cucurbit[n]urils in Hydroiodic Acid Using Potassium Iodide as an Added Template.

Glycoluril (1.49 g), hydroiodic acid (57% w/v, 6.9 mL) and potassium iodide (825 mg) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 67% |
| cucurbit[6]uril | 22% |
| cucurbit[7]uril | 10% |
| cucurbit[8]uril | 1% |
| cucurbit[9]uril | <1% |
| cucurbit[10]uril | <1% |
| cucurbit[11]uril | <1% |

Example 81

Synthesis of Cucurbit[n]urils in Hydroiodic Acid Using Rubidium Iodide as an Added Template.

Glycoluril (1.49 g), hydroiodic acid (57% w/v, 6.9 mL) and rubidium iodide (1060 mg) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 34% |
| cucurbit[6]uril | 18% |
| cucurbit[7]uril | 48% |
| cucurbit[8]uril | <1% |
| cucurbit[9]uril | <1% |
| cucurbit[10]uril | <1% |
| cucurbit[11]uril | <1% |

Example 82

Synthesis of Cucurbit[n]urils in Hydroiodic Acid Using Caesium Iodide as an Added Template.

Glycoluril (1.49 g), hydroiodic acid (57% w/v, 6.9 mL) and caesium iodide (1300 mg) were placed in a reaction flask. Formalin (40% w/v) (1.5 mL) was added in one portion and the reaction mixture heated to 100° C. for 1 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 8% |
| cucurbit[6]uril | 36% |
| cucurbit[7]uril | 53% |
| cucurbit[8]uril | 3% |
| cucurbit[9]uril | <1% |
| cucurbit[10]uril | <1% |
| cucurbit[11]uril | <1% |

Example 83

Synthesis of Cucurbit[n]urils in Hydroiodic Acid Using Red Phosphorous as an Added Template.

Glycoluril (1.49 g), hydroiodic acid (57% w/v, 6.9 mL) and red phosphorous (1 g) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 3% |
| cucurbit[6]uril | 70% |
| cucurbit[7]uril | 23% |
| cucurbit[8]uril | 4% |
| cucurbit[9]uril | <1% |
| cucurbit[10]uril | <1% |
| cucurbit[11]uril | <1% |

Example 84

Synthesis of Cucurbit[n]urils in Hydroiodic Acid Using Lithium Iodide and Red Phosphorous as an Added Template.

Glycoluril (1.49 g), hydroiodic acid (57% w/v, 6.9 mL) and lithium iodide and red phosphorous (665 mg and 650 mg respectively) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 23% |
| cucurbit[6]uril | 6% |
| cucurbit[7]uril | 65% |
| cucurbit[8]uril | 6% |
| cucurbit[9]uril | <1% |
| cucurbit[10]uril | <1% |
| cucurbit[11]uril | <1% |

Example 85

Synthesis of Cucurbit[n]urils in Hydroiodic Acid Using Sodium Iodide and Red Phosphorous as an Added Template.

Glycoluril (1.49 g), hydroiodic acid (57% w/v, 6.9 mL) and sodium iodide and red phosphorous (745 mg and 650 mg respectively) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 57% |
| cucurbit[6]uril | 9% |
| cucurbit[7]uril | 29% |

-continued

| | |
|---|---|
| cucurbit[8]uril | 5% |
| cucurbit[9]uril | <1% |
| cucurbit[10]uril | <1% |
| cucurbit[11]uril | <1% |

Example 86
Synthesis of Cucurbit[n]urils in Hydroiodic Acid Using Potassium Iodide and Red Phosphorous as an Added Template.

Glycoluril (1.49 g), hydroiodic acid (57% w/v, 6.9 mL) and potassium iodide and red phosphorous (825 mg and 650 mg respectively) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 75% |
| cucurbit[6]uril | 11% |
| cucurbit[7]uril | 10% |
| cucurbit[8]uril | 3% |
| cucurbit[9]uril | <1% |
| cucurbit[10]uril | <1% |
| cucurbit[11]uril | <1% |

Example 87
Synthesis of Cucurbit[n]urils in Hydroiodic Acid Using Rubidium Iodide and Red Phosphorous as an Added Template.

Glycoluril (1.49 g) hydroiodic acid (57% w/v, 6.9 mL) and rubidium iodide and red phosphorous (1060 mg and 650 mg respectively) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 58% |
| cucurbit[6]uril | 20% |
| cucurbit[7]uril | 20% |
| cucurbit[8]uril | 2% |
| cucurbit[9]uril | <1% |
| cucurbit[10]uril | <1% |
| cucurbit[11]uril | <1% |

Example 88
Synthesis of Cucurbit[n]urils in Hydroiodic Acid Using Caesium Iodide and Red Phosphorous as an Added Template.

Glycoluril (1.49 g), hydroiodic acid (57% w/v, 6.9 mL) and caesium iodide and red phosphorous (1300 mg and 650 mg respectively) were placed in a reaction flask. Formalin (40% w/v) (1.5 mL) was added in one portion and the reaction mixture heated to 100° C. for 2 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 21% |
| cucurbit[6]uril | 28% |
| cucurbit[7]uril | 46% |
| cucurbit[8]uril | 5% |
| cucurbit[9]uril | <1% |
| cucurbit[10]uril | <1% |
| cucurbit[11]uril | <1% |

Example 89
Synthesis of Cucurbit[n]urils in Sulfuric Acid Using Potassium Sulfate as an Added Template.

Glycoluril (1.49 g), sulfuric acid (9 M, 6.9 mL) and potassium sulfate (436 mg) were placed in a reaction flask. Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 15% |
| cucurbit[6]uril | 66% |
| cucurbit[7]uril | 18% |
| cucurbit[8]uril | 1% |
| cucurbit[9]uril | <1% |
| cucurbit[10]uril | <1% |
| cucurbit[11]uril | <1% |

Example 90
Synthesis of Cucurbit[n]urils in Sulfuric Acid Using Potassium Sulfate as an Added Template.

Glycoluril (1.49 g), sulfuric acid (9 M, 6.9 mL) and potassium sulfate (871 mg) were placed in a reaction flask. Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 11% |
| cucurbit[6]uril | 75% |
| cucurbit[7]uril | 15% |
| cucurbit[8]uril | <1% |
| cucurbit[9]uril | <1% |
| cucurbit[10]uril | <1% |
| cucurbit[11]uril | <1% |

Example 91
Synthesis of Cucurbit[n]urils in Sulfuric Acid Using Potassium Sulfate as an Added Template.

Glycoluril (1.49 g) sulfuric acid (9 M, 6.9 mL) and potassium sulfate 1307 mg) were placed in a reaction flask.

Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 33% |
| cucurbit[6]uril | 49% |
| cucurbit[7]uril | 17% |
| cucurbit[8]uril | 2% |
| cucurbit[9]uril | <1% |
| cucurbit[10]uril | <1% |
| cucurbit[11]uril | <1% |

Example 92

Synthesis of Cucurbit[n]urils in Sulfuric Acid Using Potassium Sulfate as an Added Template.

Glycoluril (1.49 g), sulfuric acid (9 M, 6.9 mL) and potassium sulfate (4350 mg) were placed in a reaction flask. Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 23% |
| cucurbit[6]uril | 64% |
| cucurbit[7]uril | 13% |
| cucurbit[8]uril | <1% |
| cucurbit[9]uril | <1% |
| cucurbit[10]uril | <1% |
| cucurbit[11]uril | <1% |

Example 93

Synthesis of Cucurbit[n]urils in Sulfuric Acid Using Lithium Sulfate as an Added Template.

Glycoluril (1.49 g), sulfuric acid (9 M, 6.9 mL) and lithium sulfate (275 mg) were placed in a reaction flask. Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 4% |
| cucurbit[6]uril | 71% |
| cucurbit[7]uril | 13% |
| cucurbit[8]uril | 24% |
| cucurbit[9]uril | 1% |
| cucurbit[10]uril | <1% |
| cucurbit[11]uril | <1% |

Example 94

Synthesis of Cucurbit[n]urils in Sulfuric Acid Using Lithium Sulfate as an Added Template.

Glycoluril (1.49 g), sulfuric acid (9 M, 6.9 mL) and lithium sulfate (2750 mg) were placed in a reaction flask. Formalin (40% w/v) (1.5 mL) was added in one portion and the reaction mixture heated to 100° C. for 3 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 25% |
| cucurbit[6]uril | 51% |
| cucurbit[7]uril | 23% |
| cucurbit[8]uril | 1% |
| cucurbit[9]uril | <1% |
| cucurbit[10]uril | <1% |
| cucurbit[11]uril | <1% |

Example 95

Synthesis of Cucurbit[n]urils in Hydrochloric Acid Using Lithium Chloride as an Added Template.

Glycoluril (5 8), hydrochloric acid (36% w/v, 6.9 mL) and lithium chloride (746 mg) were placed in a reaction flask. Paraformaldehyde (2.2 g) was added in one portion and the reaction mixture heated to 100° C. for 4 hours. The reaction mixture was cooled and the products were precipitated by addition of methanol and collected by vacuum filtration.

Yield >98% by NMR

Approximate Yields by $^{13}$C NMR (mass % of recovered product)

| | |
|---|---|
| cucurbit[5]uril | 22% |
| cucurbit[6]uril | 37% |
| cucurbit[7]uril | 29% |
| cucurbit[8]uril | 12% |
| cucurbit[9]uril | <1% |
| cucurbit[10]uril | <1% |
| cucurbit[11]uril | <1% |

Example 96

Synthesis of Cucurbit[n]urils in p-toluenesulfonic Acid Using Lithium p-toluenesulfonate as an Added Template.

Glycoluril (400 mg), p-toluenesulfonic acid (~95% 3.5 g) and lithium p-toluenesulfonate (157 mg) were placed in a reaction flask. Formalin (40% w/v) (0.5 mL) was added in one portion and the reaction mixture heated to 100° C. for 3 hours. The reaction mixture was cooled and the products were precipitated by addition of methanol and collected by vacuum filtration.

Yield 240 mg

Approximate Yields by $^{13}$C NMR (mass % of recovered product)

| | |
|---|---|
| cucurbit[5]uril | 18% |
| cucurbit[6]uril | 45% |
| cucurbit[7]uril | 26% |
| cucurbit[8]uril | 9% |

| cucurbit[9]uril | <1% |
| cucurbit[10]uril | <1% |
| cucurbit[11]uril | <1% |

Example 97
Synthesis of Cucurbit[n]urils with Hydrochloric Acid Using Trifluoroacetic Acid as a Solvent.

Glycoluril (144 mg), hydrochloric acid (36% w/v, 1 drop) and trifluoroacetic acid (1 mL) were placed in a reaction flask. Paraformaldehyde (63 mg) was added in one portion and the reaction mixture heated to 90° C. for 3 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| cucurbit[5]uril | 46% |
| cucurbit[6]uril | 54% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 98
Synthesis of Cucurbit[n]urils with Sulfuric Acid Using Trifluoroacetic Acid as a Solvent.

Glycoluril (144 mg), sulfuric acid (98% w/v, 2 drops) and trifluoroacetic acid (1 mL) were placed in a reaction flask. Paraformaldehyde (63 mg) was added in one portion and the reaction mixture heated to 90° C. for 4 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 99
Synthesis of Cucurbit[n]urils with Hydrochloric Acid Using Trifluoroacetic Acid as a Solvent.

Glycoluril (144 mg), hydrochloric acid (36% w/v, 5 drops) and trifluoroacetic acid (1 mL) were placed in a reaction flask. Paraformaldehyde (63 mg) was added in one portion and the reaction mixture heated to 90° C. for 5 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 100
Synthesis of Cucurbit[n]urils with Hydrochloric Acid Using Trifluoroacetic Acid as a Solvent.

Glycoluril (144 mg) and trifluoroacetic acid (1 mL) were placed in a reaction flask. Dry hydrochloric acid gas was then bubbled into the solution for 15 minutes. Paraformaldehyde (63 mg) was added in one portion and the reaction mixture heated to 90° C. for 20.5 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 101
Synthesis of Cucurbit[n]urils with Hydrochloric Acid Using Trifluoroacetic Acid as a Solvent.

Glycoluril (144 mg) trifluoroacetic acid (2 mL) were placed in a reaction flask. Dry hydrochloric acid gas was then bubbled into the solution for 15 minutes. Paraformaldehyde (63 mg) was added in one portion and the reaction mixture heated to 90° C. for 25 hours The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 102
Synthesis of Cucurbit[n]urils with Sulfuric Acid Using Trifluoroacetic Acid as a Solvent.

Glycoluril (144 mg), sulfuric acid (98% w/v, 1 drop) and trifluoroacetic acid (1.5 mL) were placed in a reaction flask. Paraformaldehyde (63 mg) was added in one portion and the reaction mixture heated to 90° C. for 3 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 37% |
| cucurbit[7]uril | 39% |
| cucurbit[8]uril | 24% |
| cucurbit[9]uril | <1% |
| cucurbit[10]uril | <1% |
| cucurbit[11]uril | <1% |

Example 103
Synthesis of Cucurbit[n]urils with Sulfuric Acid Using Trifluoroacetic Acid as a Solvent.

Glycoluril (144 mg), sulfuric acid (98% w/v, 2 drops) and trifluoroacetic acid (1.5 mL) were placed in a reaction flask. Paraformaldehyde (63 mg) was added in one portion and the reaction mixture heated to 90° C. for 23 hours. The reaction mixture was cooled and the products were precipitated by addition of methanol and he collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 104
Synthesis of Cucurbit[n]urils with Sulfuric Acid Using Trifluoroacetic Acid as a Solvent.

Glycoluril (144 mg), sulfuric acid (98% w/v, 5 drops) and trifluoroacetic acid (1.5 mL) were placed in a reaction flask. Paraformaldehyde (63 mg) was added in one portion and the reaction mixture heated to 90° C. for 23 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 48% |
| cucurbit[7]uril | 32% |
| cucurbit[8]uril | 20% |
| cucurbit[9]uril | <1% |
| cucurbit[10]uril | <1% |
| cucurbit[11]uril | <1% |

Example 105
Synthesis of Cucurbit[n]urils with Sulfuric Acid Using Trifluoroacetic Acid as a Solvent.

Glycoluril (144 mg), sulfuric acid (98% w/v, 5 drops) and trifluoroacetic acid (1.5 mL) were placed in a reaction flask. Paraformaldehyde (63 mg) was added in one portion and the reaction mixture heated to 90° C. for 3 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 57% |
| cucurbit[7]uril | 28% |
| cucurbit[8]uril | 15% |
| cucurbit[9]uril | <1% |
| cucurbit[10]uril | <1% |
| cucurbit[11]uril | <1% |

Example 106
Synthesis of Cucurbit[n]urils with Sulfuric Acid Using Trifluoroacetic Acid as a Solvent.

Glycoluril (144 mg), sulfuric acid (fuming, 3 drops) and trifluoroacetic acid (1.5 mL) were placed in a reaction flask. Paraformaldehyde (63 mg) was added in one portion and the reaction mixture heated to 90° C. for 25.5 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 47% |
| cucurbit[7]uril | 34% |
| cucurbit[8]uril | 20% |
| cucurbit[9]uril | <1% |
| cucurbit[10]uril | <1% |
| cucurbit[11]uril | <1% |

Example 107
Synthesis of Cucurbit[n]urils with Sulfuric Acid Using Methanesulfonic Acid as a Solvent.

Glycoluril (144 mg), sulfuric acid (98% w/v, 1 drop) and methanesulfonic acid (1.5 mL) were placed in a reaction flask. Paraformaldehyde (63 mg) was added in one portion and the reaction mixture heated to 90° C. for 26 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 5% |
| cucurbit[6]uril | 62% |
| cucurbit[7]uril | 33% |

-continued

| | |
|---|---|
| cucurbit[8]uril | <1% |
| cucurbit[9]uril | <1% |
| cucurbit[10]uril | <1% |
| cucurbit[11]uril | <1% |

Example 108
Synthesis of Cucurbit[n]urils with Sulfuric Acid Using Methanesulfonic Acid as a Solvent.

Glycoluril (144 mg), sulfuric acid (98% w/v, 5 drops) and methanesulfonic acid (1.5 mL) were placed in a reaction flask. Paraformaldehyde (63 mg) was added in one portion and the reaction mixture heated to 90° C. for 26 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 7% |
| cucurbit[6]uril | 61% |
| cucurbit[7]uril | 32% |
| cucurbit[8]uril | <1% |
| cucurbit[9]uril | <1% |
| cucurbit[10]uril | <1% |
| cucurbit[11]uril | <1% |

Example 109
Synthesis of Cucurbit[n]urils with Sulfuric Acid Using Trifluoroacetic Acid as a Solvent.

Glycoluril (144 m), sulfuric acid (fuming, 3 drops) and trifluoroacetic acid (1.5 mL) were placed in a reaction flask. Paraformaldehyde (63 mg) was added in one portion and the reaction mixture heated to 90° C. for 26 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 47% |
| cucurbit[7]uril | 35% |
| cucurbit[8]uril | 17% |
| cucurbit[9]uril | <1% |
| cucurbit[10]uril | <1% |
| cucurbit[11]uril | <1% |

Example 110
Synthesis of Cucurbit[n]urils with Sulfuric Acid Using Trifluoroacetic Acid as a Solvent.

Glycoluril (144 mg), sulfuric acid (fuming, 3 drops) and trifluoroacetic acid (1.5 mL) were placed in a reaction flask. Paraformaldehyde (63 mg) was added in one portion and the reaction mixture heated to 90° C. for 26 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | <1% |
| cucurbit[6]uril | 47% |
| cucurbit[7]uril | 32% |
| cucurbit[8]uril | 21% |
| cucurbit[9]uril | <1% |
| cucurbit[10]uril | <1% |
| cucurbit[11]uril | <1% |

Example 111
Synthesis of Cucurbit[n]urils with Sulfuric Acid Using 1,1,1-trifluoroethanol as a Solvent.

Glycoluril (144 mg), sulfuric acid (98% w/v, 1 drop) and 1,1,1-trifluoroethanol (1.5 mL) were placed in a reaction flask. Paraformaldehyde (63 m) was added in one portion and the reaction mixture heated to 90° C. for 25 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 17% |
| cucurbit[6]uril | 72% |
| cucurbit[7]uril | 11% |
| cucurbit[8]uril | <1% |
| cucurbit[9]uril | <1% |
| cucurbit[10]uril | <1% |
| cucurbit[11]uril | <1% |

Example 112
Synthesis of Cucurbit[n]urils with Sulfuric Acid Using 1,1,1-trifluoroethanol as a Solvent.

Glycoluril (144 mg), sulfuric acid (98% w/v, 5 drops) and 1,1,1-trifluoroethanol (1.5 mL) were placed in a reaction flask. Paraformaldehyde (63 mg) was added in one portion and the reaction mixture heated to 90° C. for 25 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 89% |
| cucurbit[6]uril | 11% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 113
Synthesis of Cucurbit[n]urils with Sulfuric Acid Using 1,1,1-trifluoroethanol as a Solvent.

Glycoluril (144 mg), sulfuric acid (98% w/v, 1 drop) and 1,1,1-trifluoroethanol (1.5 mL) were placed in a reaction flask. Paraformaldehyde (63 mg) was added in one portion and the reaction mixture heated to 90° C. for 170 hours. The reaction mixture was cooled and the products were pecipitated by addition of ethanol and the collected solid was then dried at 80° C. overnight and analysed by $^{13}$C NMR.

Yield >98% by NMR

Approximate Yields by $^{13}C$ NMR (mass % of recovered product)

| | |
|---|---|
| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 114
Synthesis of Cucurbit[n]urils with Sulfuric Acid Using 1,1,1-trifluoroethanol as a Solvent.

Glycoluril (144 mg), sulfuric acid (98% w/v, 5 drops) and 1,1,1-trifluoroethanol (1.5 mL) were placed in a reaction flask. Paraformaldehyde (63 mg) was added in one portion and the reaction mixture heated to 90° C. for 170 hours. The reaction mixture was cooled and the products were pecipitated by addition of ethanol and the collected solid was then dried at 80° C. overnight and analysed by $^{13}C$ NMR.

Yield >98% by NMR

Approximate Yields by $^{13}C$ NMR (mass % of recovered product)

| | |
|---|---|
| cucurbit[5]uril | <1% |
| cucurbit[6]uril | 100% |
| cucurbit[7]uril | <1% |
| cucurbit[8]uril | <1% |
| cucurbit[9]uril | <1% |
| cucurbit[10]uril | <1% |
| cucurbit[11]uril | <1% |

Example 115
Synthesis of Cucurbit[n]urils with Sulfuric Acid Using Trifluoro Acetic Acid as a Solvent and o-carborane as a Template.

Glycoluril (144 mg), sulfuric acid (98% w/v, 1 drop), o-carborane (18 mg) and trifluoro acetic acid (1.5 mL) were placed in a reaction flask. Paraformaldehyde (63 mg) was added in one portion and the reaction mixture heated to 90° C. for 25.5 hours. The reaction mixture was cooled and the products were precipitated by addition of methanol and the collected solid was then dried at 80° C. overnight and analysed by $^{13}C$ NMR.

Yield >98% by NMR

Approximate Yields by $^{13}C$ NMR (mass % of recovered product)

| | |
|---|---|
| cucurbit[5]uril | <1% |
| cucurbit[6]uril | 57% |
| cucurbit[7]uril | 32% |
| cucurbit[8]uril | 11% |
| cucurbit[9]uril | <1% |
| cucurbit[10]uril | <1% |
| cucurbit[11]uril | <1% |

Example 116
Synthesis of Cucurbit[n]urils with Sulfuric Acid Using Trifluoro Acetic Acid as a Solvent and o-carborane as a Template.

Glycoluril (144 mg), sulfuric acid (98% w/v, 5 drops), o-carborane (18 mg) and trifluoro acetic acid (1.5 mL) were placed in a reaction flask. Paraformaldehyde (63 mg) was added in one portion and the reaction mixture heated to 90° C. for 25.5 hours. The reaction mixture was cooled and the products were precipitated by addition of methanol and the collected solid was then dried at 80° C. overnight and analysed by $^{13}C$ NMR.

Yield >99% by NMR

Approximate Yields by $^{13}C$ NMR (mass % of recovered product)

| | |
|---|---|
| cucurbit[5]uril | <1% |
| cucurbit[6]uril | 50% |
| cucurbit[7]uril | 32% |
| cucurbit[8]uril | 17% |
| cucurbit[9]uril | <1% |
| cucurbit[10]uril | <1% |
| cucurbit[11]uril | <1% |

Example 117
Synthesis of Cucurbit[n]urils with Sulfuric Acid Using Trifluoro Acetic Acid as a Solvent and o-carborane as a Template.

Glycoluril (144 mg), sulfuric acid (98% w/v, 1 drop), o-carborane (18 m) and trifluoro acetic acid (1.5 mL) were placed in a reaction flask. Paraformaldehyde (63 mg) was added in one portion and the reaction mixture heated to 90° C. for 20 hours. The reaction mixture was cooled and the products were precipitated by addition of methanol and the collected solid was then dried at 80° C. overnight and analysed by $^{13}C$ Yield >98% by NMR Approximate Yields by $^{13}C$ NMR (mass % of recovered product)

| | |
|---|---|
| cucurbit[5]uril | <1% |
| cucurbit[6]uril | 51% |
| cucurbit[7]uril | 39% |
| cucurbit[8]uril | 10% |
| cucurbit[9]uril | <1% |
| cucurbit[10]uril | <1% |
| cucurbit[11]uril | <1% |

Example 118
Synthesis of Cucurbit[n]urils with Sulfuric Acid Using Trifluoro Acetic Acid as a Solvent and o-carborane as a Template.

Glycoluril (144 mg), sulfuric acid (98% w/v, 5 drops), o-carborane (18 mg) and trifluoro acetic acid (1.5 mL) were placed in a reaction flask. Paraformaldehyde (63 mg) was added in one portion and the reaction mixture heated to 90° C. for 20 hours. The reaction mixture was cooled and the products were precipitated by addition of methanol and the collected solid was then dried at 80° C. overnight and analysed by $^{13}C$ NMR.

Yield >98% by NMR

Approximate Yields by $^{13}C$ NMR (mass % of recovered product)

| | |
|---|---|
| cucurbit[5]uril | <1% |
| cucurbit[6]uril | 47% |
| cucurbit[7]uril | 38% |

-continued

| | |
|---|---|
| cucurbit[8]uril | 15% |
| cucurbit[9]uril | <1% |
| cucurbit[10]uril | <1% |
| cucurbit[11]uril | <1% |

Example 119
Synthesis of Cucurbit[n]urils with Sulfuric Acid Using Trifluoro Acetic Acid as a Solvent and o-carborane as a Template.

Glycoluril (710 mg), sulfuric acid (98% w/v, 7.5 mL), o-carborane (18 mg) and trifluoro acetic acid (1 5 mL) were placed in a reaction flask. Paraformaldehyde (63 mg) was added in one portion and the reaction mixture heated to 90° C. for 24.5 hours. The reaction mixture was cooled and the products were precipitated by addition of methanol and the collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 3% |
| cucurbit[6]uril | 53% |
| cucurbit[7]uril | 33% |
| cucurbit[8]uril | 11% |
| cucurbit[9]uril | <1% |
| cucurbit[10]uril | <1% |
| cucurbit[11]uril | <1% |

Example 120
Synthesis of Cucurbit[n]urils with Sulfuric Acid Using Methanesulfonic Acid as a Solvent and o-carborane as a Template.

Glycoluril (144 mg), sulfuric acid (98% w/v, 1 drop), o-carborane (18 mg) and methanesulfonic acid (7.5 mL) were placed in a reaction flask. Paraformaldehyde (63 mg) was added in one portion and the reaction mixture heated to 90° C. for 22.5 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 7% |
| cucurbit[6]uril | 53% |
| cucurbit[7]uril | 30% |
| cucurbit[8]uril | 10% |
| cucurbit[9]uril | <1% |
| cucurbit[10]uril | <1% |
| cucurbit[11]uril | <1% |

Example 121
Synthesis of Cucurbit[n]urils with Sulfuric Acid Using Methanesulfonic Acid as a Solvent and o-carborane as a Template.

Glycoluril (144 mg), sulfuric acid (98% w/v, 5 drops), o-carborane (18 mg) and methanesulfonic acid (1.5 mL) were placed in a reaction flask Paraformaldehyde (63 mg) was added in one portion and the reaction mixture heated to 90° C. for 22.5 hours. The reaction mixture was cooled and the products were pecipitated by addition of ethanol and collected using a centrifuge. The collected solid was then dried at 80° C. overnight and analysed by $^{13}$C NMR.

Yield >98% by NMR

Approximate Yields by $^{13}$C NMR (mass % of recovered product)

| | |
|---|---|
| cucurbit[5]uril | 6% |
| cucurbit[6]uril | 56% |
| cucurbit[7]uril | 30% |
| cucurbit[8]uril | 8% |
| cucurbit[9]uril | <1% |
| cucurbit[10]uril | <1% |
| cucurbit[11]uril | <1% |

Example 122
Preparation of Substituted Cucurbiturils

Substituted glycolurils of the following formulae were used in this synthesis:

Examples of Mixed Cucurbit[s,u]urils

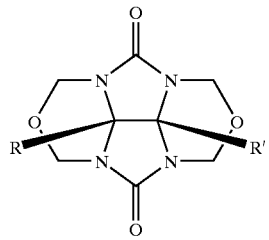

'tetracyclic diether' R=R'=CH$_3$, dimethyl; R=R'=C$_6$H$_5$, diphenyl;

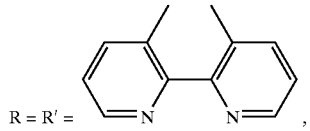

dihydrophenathroline.

(1) A mixture of the dimethyl tetracyclic diether (107 mg) and caesium chloride (71 mg) in concentrated hydrochloric acid (0.5 ml) was heated at 100° C. for 1 hr 40 mins, to give a >85% yield of the decamethylcucurbit[5]uril and <1% of the other sizes.

(2) A mixture of the dimethyl tetracyclic diether (97 mg) and glycoluril (54 mg) in concentrated hydrochloric acid (0.5 ml) was shaken at room temperature for 1 hr then heated at 100° C. for 1 hr 40 mins., at which time reaction was complete. The yield was determined by $^{13}$C NMR to be >95% for a mixture of the methyl substituted cucurbit[s,u]urils, where s,u equals 1,4; 2,3; 3,2; 4,1; 1,5; 2,4; 3,3; 4,2; 5,1; 1,6; 2,5; 3,4; 4,3; 5,2; 6,1; and s represents the unit carrying the substitution. The composition of s to u was determined by ES-MS.

(3) A mixture of the dimethyl tetracyclic diether (119 mg) glycoluril (66 mg) and caesium chloride (78 mg) in concentrated hydrochloric acid (0.5 ml) was shaken at room temperature for 1 hr then heated at 100° C. until the reaction was complete at 1 hr 20 mins. The yield by $^{13}$C NMR was near quantitative. The composition of s to u was observed to be different but not accurately determined.

(4) The diphenyl tetracyclic diether (1.9 gm), gylcoluril (0.71 gm) and para toluene sulphonic acid (10.4 gm) were combined and heated to 120° C. for 3 hr. While still hot the mixture was poured into methanol (150 ml) and precipitate collected by filtration. The solid material collected was dissolved in a minimum volume of hot formic acid and this solution was poured into hot water and the precipitate collected to give 1.32 gm of the phenyl substituted cucurbit[s,u]urils, where s,u equals 1,4; 2,3; 2,4; 3,3 and s represents the unit carrying the substitution.

(6) To a suspension of the dihydrophenathroline glycoluril (530 mg) in aqueous 40% formaldehyde was added 8M hydrochloric acid (1.8 ml) and the mixture stirred at room temperature for 5 hr. Then glycoluril (253 mg) was added and the mixture heated at 100° C. for 3hr. $^{13}$C NMR of the mixture indicated a 20–30% formation of the dihydrophenanthroline substituted cucurbit[s,u]urils.

Variations of these methods could conceivably be applied to any substituted glycoluril where the side chain is stable to the reaction conditions.

Template Function.

The controlling factors for achieving the synthesis of a variety of cucurbiturils of differing unit sizes are postulated to be primarily derived from a templating effect. For example, an anion is apparently held in position by a metal cation or the ammonium ion. The metal cations coordinate to the carbonyls of the forming cucurbituril intermediates (such as F, G1 and G2) or in the case of the ammonium cation is held through hydrogen bonding to the carbonyls of these intermediates. The larger iodide anion and its tight pairing with the lithium cation favours cucurbit[7]uril but for the more diffuse ion pairs of sodium, potassium, or rubidium, iodide does not control the size by templating around the anion but rather templating is predominantly controlled by the cation although this effect diminishes as the anion decreases in size. There has been found a common trend where the equilibrium shifts by varying combinations of anion and cations. The proton from the acid not only serves as a catalyst but also acts as a cation capable of hydrogen bonding to the carbonyls of the forming cucurbit[n]uril and also controlling the placement of anions. The degree of the competing influence between these protons and any added cations affects the equilibrium and hence the product distribution. Cucurbit[n]urils where n>7 appears to be controlled by a templating around a cation/anion cluster rather than a single ion, pair. Electrospray mass spectroscopy of larger cucurbiturils supports this showing multi charged cationic complexes.

Further influences upon the equilibrium and hence the product out come is the precipitation of product complexes. For example increasing the concentration by 10 times of a cation such as lithium in sulphuric acid chances the relative proportion of cucurbit[5]uril from 5% to 25% as a consequence of the precipitation of the cucurbit[5]uril lithium complexes.

In addition to equilibrium shifts caused by chances to the cation concentration the equilibrium is also affected by the formation of the cucurbit[6]uril iodine complex which occurs under the reaction conditions where hydriodic acid is used and hydriodic acid decomposes to form iodine. The addition of red phosphorus eliminates this effect by the in situ reduction of the iodine generated.

In addition, we have found that a wide range of other inorganic and organic compounds can be used as templates. These affect the equilibrium through a variety of subtle effects including ion-dipole, diople-diople and hydrogen bonding, hydrophobic and weak Van der Waals interactions. In essence, any material or compound stable to the reaction conditions could act as a potential template.

INDUSTRIAL APPLICABILITY

The potential uses for cucurbit[n]urils are large with academic, industrial, analytical and pharmaceutical applications. As a class these molecules can be favourable compared to the cyclodextrins because both molecular systems posses a hydrophobic cavity with polar end caps. Cyclodextrins have been used in a wide range of applications including slow release drugs, odour entrapment agents in plastic films, and enzimimics for synthesis. It is believed that cucurbit[n]urils will be of use in similar areas where benefit can be taken of the ability of the cucurbit[n]urils to take up molecules or compounds into there central cavity. Such potential uses may include: Environmental (Water and Soil)

Remediation, by the binding of polluting products and their removal;

Preventative, eg, by binding of potential pollutants before wastes are released to the environment;

Uses in biodegradable polymers.

Domestic and Public

Incorporation into polymers as odourisers, releasing fragrances slowly over time;

Or incorporated into polymers to trap unpleasant odours or toxic vapours

Encaptulation of bleaching and whitening agents.

Food

Flavour enhancers;

Flavour optimisers, hence hiding unpleasant flavours;

Polyphenol removal to reduce discolouration of juices.

Pharmaceutical

Slow release drugs, limiting side effects and reducing the frequency of doses;

Increasing drug stability in vivo or on the shelf;

Detoxification, for example, decreasing stomach irritations, or the treatment of chemical allergens by encaptulation.

Agricultural/horticultural

Slow release of herbicides and pesticides;

Stabilisation of agricultural chemicals against light and heat.

Manufacturing

Enzyme/catalyst mimics;

Regioselective control over reaction products;

Manipulation of paint and polymer products;

Chromatographic columns for chemical purification;

Analytical tools and devices;

Printing and photography.

Miscellaneous

Volatility reduction, for storage, safety, or use;

Uses for insensitive munitions manufacture;

Forensic science.

Cucurbit[n]urils are thermally more robust than cyclodextrins and are stable to strong acid solutions unlike cyclodextrins.

The present inventors have also found that cucurbit[6]uril and cucurbit[7]uril can both bind dioxane aqueous solutions. This dioxane binding properly can form the basis of processes for the removal of dioxane. According to a further aspect of the present invention, the present invention provides a process for removing dioxane from a fluid comprising contacting the fluid with cucurbit[6]uril and/or cucurbit[7]uril.

The physical removal of dioxane could take place using one of the following techniques:

Cucurbit[6 or 7]uril bound to a non-reactive solid support (silica or alumina) where the dioxane would bind to the cucurbit[6 or 7]uril and then be removed from solution by simple filtration to collect the solid support.

A solution of cucurbit[6 or 7]uril placed in dialysis tubing which would allow the passage of dioxane into the solution where it would be bound by the cucurbit[6 or 7]uril.

Incorporation of the cucurbit[6 or 7]uril into a solid clay support and use filtration techniques to remove bound dioxane.

Incorporation into a polymer film. In this case the dioxane would be entrapped by the cucurbit[6 or 7]uril inside the polymer film. When the capacity of the film has been reached it is simply removed from contact with the product stream.

In all cases the material itself could be regenerated for repeated use.

If the dioxane is contained in the solid, for example in dioxane/contaminated soil, the process of this aspect of the invention may comprise the further step of washing the soil with a fluid to thereby cause the dioxane to go into the fluid and subsequently treating the fluid in accordance with this aspect of the invention.

Cucurbit[5]uril has shown uptake of carbon monoxide. Accordingly, the invention further provides a method for removing carbon monoxide from a liquid or vapour containing carbon monoxide by contacting the liquid or vapour with cucurbit[5]uril.

The present invention provides a method for producing a range of cucurbit[n]urils and cucurbit[s,u]urils. The synthesis method results in the production of a number of cucurbit[n]urils and cucurbit[s,u]urils that have never before been produced or isolated. Separation is possible via chromatography and/or selective precipitation. The product cucurbit[n]urils and cucurbit[s,u]urils are stable to vigorous reaction conditions over a wide range of pH values. They are soluble in aqueous acid or aqueous salt solutions. The method gives cucurbiturils in much larger yields than previously possible. The use of templating compounds allows a degree of control over the relative amounts of the different cucurbit[n]urils being produced.

Those skilled in the art will appreciate that the invention described herein may be susceptible to variation and modifications other than those specifically described. It is to be understood that the present invention encompasses all such variations and modifications that fall within its spirit and scope.

What is claimed is:

1. A method for producing a cucurbit[n]uril, where n is 4, 5, 6, 7, 8, 9, 10, 11 or 12, but excluding decamethylcucurbit[5]uril and unsubstituted cucurbit[6]uril, comprising mixing substituted and/or unsubstituted glycoluril with an acid and a compound that can form methylene bridges between glycoluril units, and heating the mixture to a temperature of from 20° to 120° C. to thereby form a cucurbit[n]uril.

2. A method for producing a mixture of two or more cucurbit[n]urils, where n is from 4 to 12, comprising mixing substituted and/or unsubstituted glycoluril with an acid and a compound that can form methylene bridges between glycoluril units, and heating the mixture to a temperature of from 20° to 120° C. to thereby form a mixture of two or more cucurbit[n]urils.

3. A method as claimed in claim 2 wherein n is from 4 to 10.

4. A method as claimed in claim 2 further comprising adding a templating compound to the mixture.

5. A method as claimed in claim 4 wherein said templating compound is selected from ammonium chloride, lithium chloride, sodium chloride, potassium chloride, rubidium chloride, caesium chloride, ammonium chloride, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoaniline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobenzaldehyde, 2-aminobenzimidazole, bis-(4,4'-bipyridyl)-$\alpha,\alpha'$-p-xylene, red phosphorus, and lithium p-toluenesulfonate.

6. A method as claimed in claim 4 wherein the templating compound is a salt.

7. A method as claimed in claim 6 wherein the anion of the salt corresponds to the anion of the acid in the mixture.

8. A method as claimed in claim 4 wherein two or more templating compounds are added to the mixture.

9. A method as claimed in claim 2 wherein the acid comprises a strong mineral acid or a strong organic acid.

10. A method as claimed in claim 2 wherein the acid is selected from sulfuric acid, hydrochloric acid, hydrobromic acid, hydriodic acid, deuterated sulfuric acid, phosphoric acid, p-toluenesulfonic acid, and methane sulfonic acid.

11. A method as claimed in claim 2 further comprising adding a solvent to the reaction mixture.

12. A method as claimed in claim 11 wherein the solvent is selected from trifluoroacetic acid, methanesulfonic acid and 1,1,1-trifluoroethanol.

13. A method as claimed in claim 2 wherein the compound that can form methylene bridges between glycoluril units comprises formaldehyde, paraformaldehyde, trioxane or one or more precursors for formaldehyde.

14. A method as claimed in claim 2 wherein the mixture is heated to a temperature of from 20° C. to 110° C.

15. A method as claimed in claim 14 wherein the mixture is heated to a temperature of from 60° to 110° C.

16. A method as claimed in claim 14 wherein the mixture is heated to a temperature of from 80° to 110° C.

17. A method as claimed in claim 2, wherein the mixture is heated for between 1 hour and 24 hours.

18. A method as claimed in claim 2 wherein the acid has a concentration of at least 5 M.

19. A method as claimed in claim 2 wherein the mixture is allowed to stand at room temperature until a gel is formed prior to heating.

20. A method for producing a substituted cucurbituril of the formula cucurbit[s,u]uril, where s=number of substituted glycoluril units, u=number of unsubstituted glycoluril units and s+u=4 to 12, but excluding decamethylcucurbit[5]uril, comprising mixing substituted glycoluril and unsubstituted glycoluril with an acid and a compound that can form methylene bridges between glycoluril units and heating the mixture to a temperature of from 20° to 120° C. to thereby form a cucurbit[s,u]uril.

21. A method as claimed in claim 20 wherein the substituted glycoluric has a formula

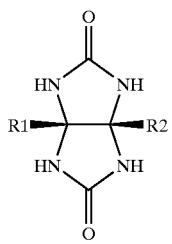

wherein $R_1$ and $R_2$ are the same or different and are selected from an optionally substituted straight chain, branched or cyclic, saturated or unsaturated hydrocarbon radical or a heterocyclyl radical or $R_1$ and $R_2$ form a cyclic hydrocarbon radical.

22. A method as claimed in claim 21 wherein $R_1$ and $R_2$ are the same or different and are selected from alkyl, alkenyl, alkynyl, aryl and heterocyclyl radicals.

23. A method as claimed in claim 20 wherein s+u=4 to 10.

24. A method as claimed in claim 20 further comprising adding a templating compound to the mixture.

25. A method as claimed in claim 24 wherein said templating compound is selected from ammonium chloride, lithium chloride, sodium chloride, potassium chloride, rubidium chloride, caesium chloride, ammonium chloride, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoaniline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobenzaldehyde, 2-aminobenzimidazole, bis-(4,4'-bipyridyl)-α,α'-p-xylene, red phosphorus, and lithium p-toluenesulfonate.

26. A method as claimed in claim 24 where said templating compound is a salt.

27. A method as claimed in claim 26 wherein the anion of the salt corresponds to the anion of the acid in the mixture.

28. A method as claimed in claim 24 wherein two or more templating compounds are added to the mixture.

29. A method as claimed in claim 20 wherein the acid comprises a strong mineral acid or a strong organic acid.

30. A method as claimed in claim 20 wherein the acid is selected from sulfuric acid, hydrochloric acid, hydrobromic acid, hydroiodic acid, deuterated sulfuric acid, phosphoric acid, p-toluenesulfonic acid, and methane sulfonic acid.

31. A method as claimed in claim 20 further comprising adding a solvent to the mixture.

32. A method as claimed in claim 31 wherein the solvent is selected from trifluoroacetic acid, methane sulfonic acid and 1,1,1-trifluoroethanol.

33. A method as claimed in claim 20 wherein the compound that can form methylene bridges between glycoluril units comprises formaldehyde, paraformaldehyde, trioxane or one or more precursors for formaldehyde.

34. A method as claimed in claim 20 wherein the mixture is heated to a temperature of from 20° to 110° C.

35. A method as claimed in claim 34 wherein the mixture is heated to a temperature of from 60° to 110° C.

36. A method as claimed in claim 34 wherein the mixture is heated to a temperature of from 80° to 110° C.

37. A method as claimed in claim 20 wherein the mixture is heated for between 1 hour and 24 hours.

38. A method as claimed in claim 20 wherein the acid has a concentration of at least 5M.

39. A method as claimed in claim 20 wherein the mixture is allowed to stand at room temperature until a gel is formed prior to heating.

40. A method for separating a mixture of cucurbit[n]urils, where n=4 to 12, by mixing the mixture of cucurbit[n]urils with a salt solution, in which at least one of the cucurbit[n]urils, but not all of the cucurbit[n]urils, dissolves, and separating solids from the solution.

41. A method as claimed in claim 40 further comprising recovering at least one cucurbit[n]uril from the solids.

42. A method as claimed in claim 40 further comprising recovering at least one cucurbit[n]uril from solution.

43. A method as claimed in claim 42 further comprising passing the solution into contact with an ion exchange resin to thereby absorb dissolved cucurbit[n]urils onto the resin and subsequently eluting said cucurbit[n]urils from the resin.

44. A method for separating a mixture of cucurbit[n]urils, where n=4 to 10, by dissolving the mixture of cucurbit[n]urils and subjecting the thus-formed solution of cucurbit[n]urils to chromatographic separation.

45. A method for separating a mixture of cucurbit[s,u]urils where s=number of substituted glycoluril units, u=number of unsubstituted glycoluril units and s+u=4 to 12 comprising dissolving the mixture of cucurbit[s,u]urils and subjecting the thus-formed mixture of cucurbit[s,u]urils to chromatographic separation.

46. Cucurbit[n]uril, where n=4 to 12, excluding unsubstituted cucurbit[6]uril and decamethylcucurbit[5]uril.

47. Substituted cucurbiturils of the formula cucurbit[s,u]uril, wherein s=number of substituted glycoluril units and u=number of unsubstituted glycoluril units and s+u=4 to 12, but excluding decamethylcucurbit[5]uril.

48. A substituted glycoluril of the formula:

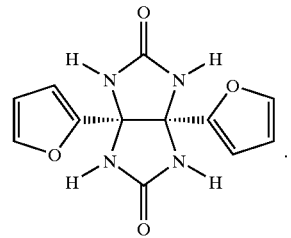

49. A substituted glycoluril of the formula:

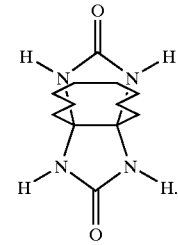

50. A cucurbit[n]uril of the formula (I):

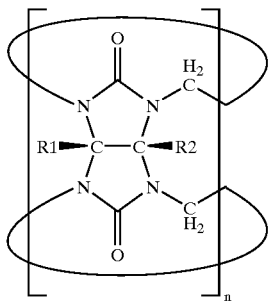

wherein n=4 to 12,
and wherein, for each unit of the formula (II)

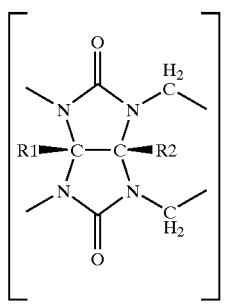

making up the cucurbit[n]uril, $R_1$ and $R_2$ are independently selected from H, an optionally substituted straight chain, branched or cyclic, saturated or unsaturated hydrocarbon radical or a heterocyclyl radical, or $R_1$ and $R_2$ form a cyclic hydrocarbon radical, but excluding unsubstituted cucurbit[6]uril and decamethylcucurbit[5]uril.

51. A cucurbit[n]uril according to claim 50 wherein for each unit of the formula (II) making up the cucurbit[n]uril, $R_1$ and $R_2$ are both H, and n is 4, 5, 7, 8, 9, 10, 11 or 12.

52. A cucurbit[n]uril according to claim 50, wherein for each unit of the formula (II) making up the cucurbituril, $R_1$ and $R_2$ are both H, or $R_1$ and $R_2$ are independently selected from an optionally substituted straight chain, branched or cyclic, saturated or unsaturated hydrocarbon radical or a heterocyclyl radical, or $R_1$ and $R_2$ form a cyclic hydrocarbon radical.

53. A method for producing a cucurbit[n]uril of the formula (I) as defined in claim 50, but excluding unsubstituted cucurbit[6]uril and decamethylcucurbit[5]uril, the method comprising mixing a glycoluril of the formula (III), or two or more glycolurils of the formula (III),

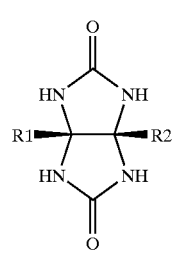

wherein $R_1$ and $R_2$ are independently selected from H, an optionally substituted straight chain, branched or cyclic, saturated or unsaturated hydrocarbon radical or a heterocyclyl radical, or $R_1$ and $R_2$ form a cyclic hydrocarbon radical, with an acid and a compound that can form methylene bridges between glycoluril units, and heating the mixture to a temperature of from 20° to 120° C. to thereby form a cucurbit[n]uril of formula (I).

54. A method as claimed in claim 53, wherein $R_1$ and $R_2$ are the same or different and are selected from alkyl, alkenyl, alkynyl, aryl and heterocyclyl radicals.

55. A method as claimed in claim 53, wherein $R_1$ and $R_2$ are H.

56. A method as claimed in claim 53, wherein n=4 to 10.

57. A method as claimed in claim 53, further comprising adding a templating compound to the mixture.

58. A method as claimed in claim 57, wherein said templating compound is selected from ammonium chloride, lithium chloride, sodium chloride, potassium chloride, rubidium chloride, caesium chloride, ammonium chloride, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoaniline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobenzaldehyde, 2-aminobenzimidazole, bis-(4,4'-bipyridyl)-α,α'-p-xylene, red phosphorus, and lithium p-toluenesulfonate.

59. A method as claimed in claim 57 wherein said templating compound is a salt.

60. A method as claimed in claim 59 wherein the anion of the salt corresponds to the anion of the acid in the mixture.

61. A method as claimed in claim 57 wherein two or more templating compounds are added to the mixture.

62. A method as claimed in claim 53 wherein the acid comprises a strong mineral acid or a strong organic acid.

63. A method as claimed in claim 53 wherein the acid is selected from sulfuric acid, hydrochloric acid, hydrobromic acid, hydriodic acid, deuterated sulfuric acid, phosphoric acid, p-toluenesulfonic acid, and methane sulfonic acid.

64. A method as claimed in claim 53 further comprising adding a solvent to the mixture.

65. A method as claimed in claim 64 wherein the solvent is selected from trifluoroacetic acid, methane sulfonic acid and 1,1,1-trifluoroethanol.

66. A method as claimed in claim 53 wherein the compound that can form methylene bridges between glycoluril units comprises formaldehyde, paraformaldehyde, trioxane or one or more precursors for formaldehyde.

67. A method as claimed in claim 53 wherein the mixture is heated to a temperature of from 20° to 110° C.

68. A method as claimed in claim 67 wherein the mixture is heated to a temperature of from 60° to 110° C.

69. A method as claimed in claim 67 wherein the mixture is heated to a temperature of from 80° to 110° C.

70. A method as claimed in claim 53 wherein the mixture is heated for between 1 hour and 24 hours.

71. A method for producing a cucurbit[n]uril, where n is 4 to 12, comprising mixing a diether of formula 2, or two or more diethers of the formula 2, (2)

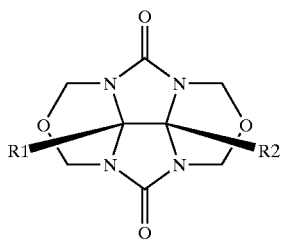

wherein $R_1$ and $R_2$ are independently selected from H, an optionally substituted straight chain, branched or cyclic, saturated or unsaturated hydrocarbon radical or a heterocyclyl radical, or $R_1$ and $R_2$ form a cyclic hydrocarbon radical, and optionally a glycoluril of formula (III) or two or more glycolurils of the formula (III)

(III)

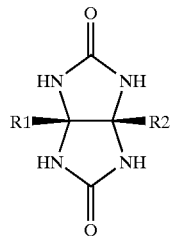

wherein $R_1$ and $R_2$ are independently selected from H, an optionally substituted straight chain, branched or cyclic, saturated or unsaturated hydrocarbon radical or a heterocyclyl radical, or $R_1$ and $R_2$ form a cyclic hydrocarbon radical, with an acid, and heating the mixture to a temperature of from 20° to 120° C. to thereby form a cucurbit[n]uril.

72. A method as claimed in claim 71 wherein the mixture is heated to a temperature of from 20° to 110° C.

73. A method as claimed in claim 72 wherein the mixture is heated to a temperature of from 60° to 110° C.

74. A method as claimed in claim 72 wherein the mixture is heated to a temperature of from 80° to 110° C.

75. A method as claimed in claim 71 wherein $R_1$ and $R_2$ are selected from alkyl, alkenyl, alkynyl, aryl and heterocyclyl radicals.

76. A method as claimed in claim 71 wherein $R_1$ and $R_2$ are H.

77. A method as claimed in claim 71 wherein n=4 to 10.

78. A method as claimed in claim 71 further comprising adding a templating compound to the mixture.

79. A method as claimed in claim 78 wherein said templating compound is selected from ammonium chloride, lithium chloride, sodium chloride, potassium chloride, rubidium chloride, caesium chloride, ammonium chloride, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoaniline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobenzaldehyde, 2-aminobenzimidazole, bis-(4,4'-bipyridyl)-α,α'-p-xylene, red phosphorus, and lithium p-toluenesulfonate.

80. A method as claimed in claim 78 wherein said templating compound is a salt.

81. A method as claimed in claim 80 wherein the anion of the salt corresponds to the anion of the acid in the mixture.

82. A method as claimed in claim 78 wherein two or more templating compounds are added to the mixture.

83. A method as claimed in claim 71 wherein the acid comprises a strong mineral acid or a strong organic acid.

84. A method as claimed in claim 71 wherein the acid is selected from sulfuric acid, hydrochloric acid, hydrobromic acid, hydriodic acid, deuterated sulfuric acid, phosphoric acid, p-toluenesulfonic acid, and methane sulfonic acid.

85. A method as claimed in claim 71 further comprising adding a solvent to the mixture.

86. A method as claimed in claim 85 wherein the solvent is selected from trifluoroacetic acid, methane sulfonic acid and 1,1,1-trifluoroethanol.

87. A method as claimed in claim 71 wherein the mixture is heated for between 1 hour and 24 hours.

88. A method for producing a cucurbit[n]uril, where n=4 to 12, comprising mixing a tetrol of the formula 1, or two or more tetrols of the formula 1, (1)

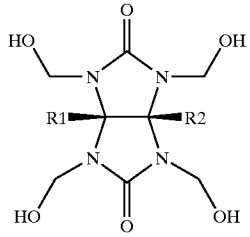

wherein $R_1$ and $R_2$ are independently selected from H, an optionally substituted straight chain, branched or cyclic, saturated or unsaturated hydrocarbon radical or a heterocyclyl radical, or $R_1$ and $R_2$ form a cyclic hydrocarbon radical, with an acid, and heating the mixture to a temperature of from 20° to 120° C. to thereby form a cucurbit[n]uril.

89. A method as claimed in claim 88 wherein the mixture is heated to a temperature of from 20° to 110° C.

90. A method as claimed in claim 89 wherein the mixture is heated to temperature of from 60° to 110° C.

91. A method as claimed in claim 89 wherein the mixture is heated to a temperature of from 80° to 110° C.

92. A method as claimed in claim 88 wherein $R_1$ and $R_2$ are selected from alkyl, alkenyl, alkynyl, aryl and heterocyclyl radicals.

93. A method as claimed in claim 88 wherein $R_1$ and $R_2$ are H.

94. A method as claimed in claim 88 wherein n=4 to 10.

95. A method as claimed in claim 88 further comprising adding a templating compound to the mixture.

96. A method as claimed in claim 95 wherein said templating compound is selected from ammonium chloride, lithium chloride, sodium chloride, potassium chloride, rubidium chloride, caesium chloride, ammonium chloride, lithium bromide, sodium bromide, potassium bromide, rubidium bromide, caesium bromide, lithium iodide, sodium iodide, potassium iodide, acbidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoaniline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobenzaldehyde, 2-aminobenzimidazole, bis-(4,4'-bipyridyl)-α,α'-p-xylene, red phosphorus, and lithium p-toluenesulfonate.

97. A method as claimed in claim 95 wherein said templating compound is a salt.

98. A method as claimed in claim 97 wherein the anion of the salt corresponds to the anion of the acid in the mixture.

99. A method as claimed in claim 95 wherein two or more templating compounds are added to the mixture.

100. A method as claimed in claim 88 wherein the acid comprises a strong mineral acid or a strong organic acid.

101. A method as claimed in claim 88 wherein the acid is selected from sulfuric acid, hydrochloric acid, hydrobromic acid, hydriodic acid, deuterated sulfuric acid, phosphoric acid, p-toluenesulfonic acid, and methane sulfonic acid.

102. A method as claimed in claim 88 further comprising adding a solvent to the mixture.

103. A method as claimed in claim 102 wherein the solvent is selected from trifluoroacetic acid, methane sulfonic acid and 1,1,1-trifluoroethanol.

104. A method as claimed in claim 88 wherein the mixture is heated for between 1 hour and 24 hours.

* * * * *